(12) United States Patent
Koivistoinen et al.

(10) Patent No.: US 9,783,809 B2
(45) Date of Patent: Oct. 10, 2017

(54) EUKARYOTIC CELL AND METHOD FOR PRODUCING GLYCOLIC ACID

(71) Applicant: Teknologian tutkimuskeskus VTT, VTT (FI)

(72) Inventors: Outi Koivistoinen, Espoo (FI); Joosu Kuivanen, Espoo (FI); Peter Richard, Espoo (FI); Merja Penttilä, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 14/348,902

(22) PCT Filed: Oct. 4, 2012

(86) PCT No.: PCT/FI2012/050956
§ 371 (c)(1),
(2) Date: Apr. 1, 2014

(87) PCT Pub. No.: WO2013/050659
PCT Pub. Date: Apr. 11, 2013

(65) Prior Publication Data
US 2014/0295510 A1  Oct. 2, 2014

Related U.S. Application Data

(60) Provisional application No. 61/542,833, filed on Oct. 4, 2011.

(30) Foreign Application Priority Data

Dec. 29, 2011  (FI) .................................. 20116334

(51) Int. Cl.
| | | |
|---|---|---|
| C12N 9/04 | (2006.01) | |
| C12N 15/00 | (2006.01) | |
| C12N 1/20 | (2006.01) | |
| C12N 1/14 | (2006.01) | |
| C12Q 1/68 | (2006.01) | |
| C12P 7/42 | (2006.01) | |
| C07H 21/04 | (2006.01) | |
| C12N 15/52 | (2006.01) | |

(52) U.S. Cl.
CPC .............. *C12N 15/52* (2013.01); *C12N 1/14* (2013.01); *C12N 9/0006* (2013.01); *C12P 7/42* (2013.01)

(58) Field of Classification Search
CPC .......... C12N 9/0006; C12N 15/80; C12P 7/42
See application file for complete search history.

(56) References Cited

U.S. PATENT DOCUMENTS

| | | | |
|---|---|---|---|
| 9,090,898 B2* | 7/2015 | Farmer | C12N 9/0006 |
| 2010/0168481 A1* | 7/2010 | Farmer | C12N 9/0006 |
| | | | 568/852 |

FOREIGN PATENT DOCUMENTS

| | | |
|---|---|---|
| JP | 54119089 A | 9/1979 |
| JP | 10174593 A | 6/1998 |
| JP | 2006067823 A | 3/2006 |
| WO | WO2007140816 | 12/2007 |
| WO | WO2010/108909 | 9/2010 |
| WO | WO2011036213 | 3/2011 |
| WO | WO2011100601 | 8/2011 |

OTHER PUBLICATIONS

Hoover et al. Characteristics of an Arabidopsis glyoxylate reductase: general biochemical properties and substrate specificity for the recombinant protein, and developmental expression and implications for glyoxylate and succinic semialdehyde metabolism in planta. Canada Journal of Botany. 85(9):883-895 (2007).*
Maris et al. Oct. 11, 2006. Alcoholic fermentation of carbon sources in biomass hydrolysates by *Saccharomyces cerevisiae*: current status.Antonie van Leeuwenhoek (2006) 90:391-41.*
Lau et al. Comparing the fermentation performance of *Escherichia coli* KO11, *Saccharomyces cerevisiae* 424A(LNH-ST) and *Zymomonas mobilis* AX101 for cellulosic ethanol production. Biotechnology for Biofules 2010, 3:11.*
Branden et al. Introduction to Protein Structure, Garland Publishing Inc., New York, p. 247, 1991.*
Q9LSV0_ARATH. UniProtKB/TrEMBL. 2011.*
GenBank AY044183. 2003.*
Breitkreuz, K. et al., "A Novel-Hydroxybutyrate Dehydrogenase: Identification and Expression of an Arabidopsis cDNA and Potential Role Under Oxygen Defiency", Journal of Biological Chemistry, vol. 278, No. 42, Oct. 1, 2003.
Kataoka, M. et al., "Glycolic acid production using ethylene glycol-oxidizing microorganisms", Biosci. Biolechnol. Biochem., 2001, vol. 65, No. 10.
Rintala, E. et al., "The ORF YNL274c (GOR1) codes for glyoxylate reductase in *Saccharomyces cerevisiae* " Yeast, 2007, vol. 24.
Hoover, G. et al., "Characteristics of an Arabidopsis glyoxylate reductase: general biochemical properties and substrate specificity for the recombinant protein, and developmental expression . . .", Canadian Journal of Botany, vol. 85, 2007.
Hoover, G. et al., "Identification of catalytically important amino acid residues for enzymatic reduction of glyoxylate in plants", Biochimica et Biophysica Acta 1834, 2013, pp. 2663-2671.

* cited by examiner

Primary Examiner — Yong Pak
(74) Attorney, Agent, or Firm — Seppo Laine Oy

(57) ABSTRACT

The present invention concerns a eukaryotic host selected from microorganisms, and a method for producing glycolic acid using said eukaryotic host cells, especially cells of a genetically modified fungal host. Further this invention relates to a glycolic acid product obtained using the method described here and the use of genetically modified microorganism cells in production of glycolic acid.

7 Claims, 11 Drawing Sheets

SEQUENCE LISTING

```
<160> NUMBER OF SEQ ID NOS: 84

<210> SEQ ID NO 1
<211> LENGTH: 1032
<212> TYPE: DNA
<213> ORGANISM: Arabidobsis thaliana

<400> SEQUENCE: 1
atggaagtag ggtttctggg tttgggaatc atgggaaaag ccatgtcaat gaatctattg      60
aagaatggat tcaaagtcac tgtatggaac agaacactct ccaagtgtga tgagcttgtg     120
gagcatggtg catctgtatg tgagagtcca gctgaagtaa tcaagaaatg caaatacact     180
attgctatgc tctctgatcc ttgtgctgct ctttcggttg ttttcgataa aggcggtgtt     240
ttggagcaga tatgtgaagg aaaaggttat atcgatatgt cgactgttga tgcagagact     300
tctttgaaga tcaatgaggc aatcaccggg aagggtggtc ggttcgtaga aggtccggtt     360
tcaggtagca aaaagccagc tgaagatggc caactcatta tccttgctgc tggtgacaag     420
gcactctttg aggaatcaat cccagctttt gatgtcttgg ggaagagatc gttttacttg     480
ggacaagttg gaaacggagc taaaatgaag ctaatagtaa acatgataat gggaagcatg     540
atgaatgcat tctctgaggg gcttgtattg gctgacaaga gtggacttag ctctgacact     600
```

```
cttttggata ttctggatct gggagcaatg actaacccga tgttcaaggg gaaaggacct      660
tcaatgacca agagtagtta cccaccagca tttccattga acatcagca gaaagacatg      720 aggctagctc ttgctcttgg cgatgaaaac gcggtttcca tgcctgtagc cgcggctgca      780
aacgaggctt ttaagaaggc gagaagcttg gactaggag atctcgactt ctctgctgtg      840
attgaagctg tgaaattctc ccgcgaatag caaactgttt caaaacatcc actcatttgg      900
attggctgag ttactgaaat cattgttatc ttcccaaata gagatttact catttggcca      960
aacacacatt ttaatccttc accaaataaa aagtcttaac cacaaaaaaa aaaaaaaaaa     1020
aaaaaaaaaa aa                                                         1032
```

<210> SEQ ID NO 2
<211> LENGTH: 873
<212> TYPE: DNA
<213> ORGANISM: Artificial Sequence
<220> FEATURE:
<223> OTHER INFORMATION: Synthetic codon optimised Arabidobsis thaliana
      glyoxylate reductase for expression in Saccharomyces cerevisiae

<400> SEQUENCE: 2

```
atggaagttg gtttcttggg tttaggtatc atgggtaaag ctatgtcaat gaatttgttg       60
aaaaatggtt tcaaggttac tgtttggaac agaacattgt ctaagtgtga tgaattggtt      120
gaacatggtg cttccgtttg tgaaagtcca gcagaagtta ttaaaaagtg taagtacact      180
atcgctatgt tgtccgatcc ttgtgctgca ttgagtgttg ttttcgataa aggtggtgtt      240
ttggaacaaa tctgtgaggg taaaggttac atcgatatgt ctaccgttga tgctgaaact      300
tcattgaaaa ttaacgaagc aatcactggt aaaggtggta gattcgttga aggtccagtt      360
tctggttcta gaaacctgc agaagatggt caattaatta ttttggctgc aggtgacaaa      420
gctttgtttg aagaatcaat tccagcattc gatgttttgg gtaaaagatc cttctatttg      480
ggtcaagttg gtaatggtgc taagatgaag ttgatcgtta acatgatcat gggttctatg      540
atgaacgctt tctcagaagg tttggtttta gcagataaat ctggtttgtc ttcagataca      600
ttgttggata tcttggattt gggtgctatg accaacccaa tgtttaaggg taaaggtcct      660
tcaatgacta agtccagtta cccacctgca ttcccattga agcatcaaca aaaggatatg      720
agattggctt tagcattggg tgacgaaaat gctgttttcta tgcctgttgc tgcagctgca      780
aacgaagctt taaaaaggc aagatcctta ggtttgggtg acttggatt cagtgctgtt      840 attgaagcag ttaaattctc tagagaatag taa                                  873
```

<210> SEQ ID NO 3
<211> LENGTH: 289
<212> TYPE: PRT
<213> ORGANISM: Arabidobsis thaliana

<400> SEQUENCE: 3

```
Met Glu Val Gly Phe Leu Gly Leu Gly Ile Met Gly Lys Ala Met Ser
1               5                   10                  15

Met Asn Leu Leu Lys Asn Gly Phe Lys Val Thr Val Trp Asn Arg Thr
            20                  25                  30

Leu Ser Lys Cys Asp Glu Leu Glu His Gly Ala Ser Val Cys Glu
        35                  40                  45

Ser Pro Ala Glu Val Ile Lys Lys Cys Lys Tyr Thr Ile Ala Met Leu
    50                  55                  60

Ser Asp Pro Cys Ala Ala Leu Ser Val Val Phe Asp Lys Gly Gly Val
```

```
                65                  70                  75                  80
Leu Glu Gln Ile Cys Glu Gly Lys Gly Tyr Ile Asp Met Ser Thr Val
                    85                  90                  95

Asp Ala Glu Thr Ser Leu Lys Ile Asn Glu Ala Ile Thr Gly Lys Gly
                100                 105                 110

Gly Arg Phe Val Glu Gly Pro Val Ser Gly Ser Lys Lys Pro Ala Glu
            115                 120                 125

Asp Gly Gln Leu Ile Ile Leu Ala Ala Gly Asp Lys Ala Leu Phe Glu
        130                 135                 140

Glu Ser Ile Pro Ala Phe Asp Val Leu Gly Lys Arg Ser Phe Tyr Leu
145                 150                 155                 160

Gly Gln Val Gly Asn Gly Ala Lys Met Lys Leu Ile Val Asn Met Ile
                165                 170                 175

Met Gly Ser Met Met Asn Ala Phe Ser Glu Gly Leu Val Leu Ala Asp
                180                 185                 190

Lys Ser Gly Leu Ser Ser Asp Thr Leu Leu Asp Ile Leu Asp Leu Gly
            195                 200                 205

Ala Met Thr Asn Pro Met Phe Lys Gly Lys Gly Pro Ser Met Thr Lys
        210                 215                 220

Ser Ser Tyr Pro Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ala Asn Glu Ala Phe Lys Lys Ala Arg Ser Leu Gly Leu
                260                 265                 270

Gly Asp Leu Asp Phe Ser Ala Val Ile Glu Val Lys Phe Ser Arg
            275                 280                 285

Glu

<210> SEQ ID NO 4
<211> LENGTH: 870
<212> TYPE: DNA
<213> ORGANISM: Artificial Sequence
<220> FEATURE:
<223> OTHER INFORMATION: Synthetic codon optimised Arabidobsis thaliana
      glyoxylate reductase for expression in Aspergillus niger

<400> SEQUENCE: 4
atggaagtcg ggttttggg tctgggtatt atggggaagg ctatgtctat gaatctcctg      60
aagaatgggt ttaaggttac ggtctggaac cgcaccctt ccaagtgcga tgagctggtc     120
gaacacggag catccgtgtg cgagagccca gctgaagtta tcaagaagtg taagtacact     180
attgctatgc tctcagatcc atgcgccgct ttgagtgtcg tgttcgacaa gggcggtgtg     240
ctcgagcaga tctgtgaagg caagggttat attgatatgt ccaccgttga cgcagagact     300
agcttgaaga tcaatgaagc gattaccggc aagggagggc gtttgttga gggaccggtc      360 tcagggagta agaagccagc cgaagatgga cagctcatca ttttggcagc ggggacaag      420 gcactcttcg aggaatctat ccccgcgttt gacgtccttg gcaagcgatc gttctacctg     480
ggtcaagttg gaaacggggc caagatgaag ctgatcgtca acatgattat gggatctatg     540
atgaatgcct ttcggaggg cttggtgctt gctgataagt ccggtttgtc cagcgacacg      600
ctgctcgata tcctggacct cggggccatg acaaatccca tgttcaaggg caagggtcct     660
tcgatgacca gtcttcgta tcccctgct ttccctca agcatcagca aaaggatatg         720
cgcttggccc ttgctctggg cgacgagaac gcagtgtcaa tgcctgttgc cgctgcagcg     780
```

```
aatgaagcat tcaagaaggc gcggtctctg ggctgggtg accttgattt ctcggcagtt    840
attgaggcgg tgaagttttc gcgtgaatga                                    870

<210> SEQ ID NO 5
<211> LENGTH: 60
<212> TYPE: DNA
<213> ORGANISM: Artificial Sequence
<220> FEATURE:
<223> OTHER INFORMATION: Synthetic oligonucleotide ScMLS1f

<400> SEQUENCE: 5
ttctacactg gctaccgatt taactcatct tcttgaaagt ctgcaggtcg acaacccta    60

<210> SEQ ID NO 6
<211> LENGTH: 63
<212> TYPE: DNA
<213> ORGANISM: Artificial Sequence
<220> FEATURE:
<223> OTHER INFORMATION: Synthetic oligonucleotide ScMLS1r

<400> SEQUENCE: 6
tcatgataag atgattcatt gctaactacg aaacgaagca cactagtgga tctgatatca    60
cct                                                                  63

<210> SEQ ID NO 7
<211> LENGTH: 60
<212> TYPE: DNA
<213> ORGANISM: Artificial Sequence
<220> FEATURE:
<223> OTHER INFORMATION: Synthetic oligonucleotide ScDaL7f

<400> SEQUENCE: 7
gagttcaatt tgtcataact tatcaggcct tatcagctca ctgcaggtcg acaacccta    60

<210> SEQ ID NO 8
<211> LENGTH: 63
<212> TYPE: DNA
<213> ORGANISM: Artificial Sequence
<220> FEATURE:
<223> OTHER INFORMATION: Synthetic oligonucleotide ScDaL7r

<400> SEQUENCE: 8
tgcagttgat atcacttaga gtatgtgtca taggcacggt cactagtgga tctgatatca    60
cct                                                                  63

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide MLS1seqf

<400> SEQUENCE: 9
tgcagtgtca gccttacga                                                 19

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide MLS1seqr

<400> SEQUENCE: 10
```
cgttgctata ctttctcgac                                         20

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide MLS2seqf

<400> SEQUENCE: 11
caaggacacc gtcattgac                                          19

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide MLS2seqr

<400> SEQUENCE: 12
cataggttta cgattatcga c                                       21

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide ScGLYRp3466-SalIf

<400> SEQUENCE: 13
gtcgacgatc tacgtatggt catttcttc                               29

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide ScGLYRp3466-SalIr

<400> SEQUENCE: 14
gtcgaccgaa ttggagctag acaaag                                  26

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonucleotide HOr-HO1f

<400> SEQUENCE: 15
agcttaatta tcctgggcac gagtga                                  26

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide HOr-HO1r

<400> SEQUENCE: 16
cataggccac tgtaagattc cgcca                                   25

<210> SEQ ID NO 17
<211> LENGTH: 56
<212> TYPE: DNA
<213> ORGANISM: Artificial Sequence

```
<220> FEATURE:
<223> OTHER INFORMATION: Synthetic oligonucleotide ICL1fwd

<400> SEQUENCE: 17
cttttcttgc ttaaatctat aactacaaaa aacacataca atgcctatcc ccgttg          56

<210> SEQ ID NO 18
<211> LENGTH: 62
<212> TYPE: DNA
<213> ORGANISM: Artificial Sequence
<220> FEATURE:
<223> OTHER INFORMATION: Synthetic oligonucleotide ICL1rev

<400> SEQUENCE: 18
cattgttcct tattcagtta gctagctgag ctcgactcta gctatttctt tacgccattt      60
tc                                                                    62

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide EcoRI-102fwd

<400> SEQUENCE: 19
ctattttccc ttcttacg                                                   18

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide BamHI+27rev

<400> SEQUENCE: 20
cgttcattgt tccttattc                                                  19

<210> SEQ ID NO 21
<211> LENGTH: 60
<212> TYPE: DNA
<213> ORGANISM: Artificial Sequence
<220> FEATURE:
<223> OTHER INFORMATION: Synthetic oligonucleotide Flank-TPI-ICL1-PolyAf

<400> SEQUENCE: 21
ccagctggcg aaaggggggat gtgctgcaag gcgattaagt gaattgggga tctacgtatg    60

<210> SEQ ID NO 22
<211> LENGTH: 60
<212> TYPE: DNA
<213> ORGANISM: Artificial Sequence
<220> FEATURE:
<223> OTHER INFORMATION: Synthetic oligonucleotide Flank-TPI-ICL1-PolyAr

<400> SEQUENCE: 22
tacattatac gaagttatat taagggttgt cgacctgcag cgaattggag ctagacaaag     60

<210> SEQ ID NO 23
<211> LENGTH: 62
<212> TYPE: DNA
<213> ORGANISM: Artificial Sequence
<220> FEATURE:
<223> OTHER INFORMATION: Synthetic oligonucleotide Flank-KanMXfwd

<400> SEQUENCE: 23
```
atacatccct tttttttttt gtctttgtct agctccaatt cgctgcaggt cgacaaccct    60
ta                                                                  62

<210> SEQ ID NO 24
<211> LENGTH: 62
<212> TYPE: DNA
<213> ORGANISM: Artificial Sequence
<220> FEATURE:
<223> OTHER INFORMATION: Synthetic oligonucleotide Flank-KanMXrev

<400> SEQUENCE: 24
accctcacta aagggaacaa aagctggagc tccaccgcgc actagtggat ctgatatcac    60
ct                                                                  62

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide Check-IDP2-del-ICL1-f

<400> SEQUENCE: 25
ctaaatcaat cttttcaat tt                                             22

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide Check-IDP2-del-ICL1-r

<400> SEQUENCE: 26
catacattat acgaagttat attaagg                                       27

<210> SEQ ID NO 27
<211> LENGTH: 61
<212> TYPE: DNA
<213> ORGANISM: Artificial Sequence
<220> FEATURE:
<223> OTHER INFORMATION: Synthetic oligonucleotide IDP2-ICL1-f

<400> SEQUENCE: 27
ccagactaat gatcaagtaa ctgtggattc tgccaccgcg agaattgggg atctacgtat    60
g                                                                   61

<210> SEQ ID NO 28
<211> LENGTH: 65
<212> TYPE: DNA
<213> ORGANISM: Artificial Sequence
<220> FEATURE:
<223> OTHER INFORMATION: Synthetic oligonucleotide IDP2-ICL1-r

<400> SEQUENCE: 28
cttttttcaa tctagattcc accgcgtcaa tgaactcctc ggcactagtg gatctgatat    60
cacct                                                               65

<210> SEQ ID NO 29
<211> LENGTH: 32
<212> TYPE: DNA
<213> ORGANISM: Artificial Sequence
<220> FEATURE:
<223> OTHER INFORMATION: Synthetic oligonucleotide ACO1HindIIIf

<400> SEQUENCE: 29
atataagctt acaatgctgt ctgcacgttc tg                              32

<210> SEQ ID NO 30
<211> LENGTH: 31
<212> TYPE: DNA
<213> ORGANISM: Artificial Sequence
<220> FEATURE:
<223> OTHER INFORMATION: Synthetic oligonucleotide ACO1HindIIIr

<400> SEQUENCE: 30
atataagctt ttatttcttc tcatcggcct t                               31

<210> SEQ ID NO 31
<211> LENGTH: 39
<212> TYPE: DNA
<213> ORGANISM: Artificial Sequence
<220> FEATURE:
<223> OTHER INFORMATION: Synthetic oligonucleotide ADH2delflankKpnINotIf

<400> SEQUENCE: 31
atataggtac cgcggccgcc catgtctaca gtttagagg                       39

<210> SEQ ID NO 32
<211> LENGTH: 39
<212> TYPE: DNA
<213> ORGANISM: Artificial Sequence
<220> FEATURE:
<223> OTHER INFORMATION: Synthetic oligonucleotide
     ADH2delflankEcoRISalIr

<400> SEQUENCE: 32
atatagaatt cgtcgaccgg atctcttatg tctttacga                       39

<210> SEQ ID NO 33
<211> LENGTH: 39
<212> TYPE: DNA
<213> ORGANISM: Artificial Sequence
<220> FEATURE:
<223> OTHER INFORMATION: Synthetic oligonucleotide
     ADH2delflank2EcoRIBamHIf

<400> SEQUENCE: 33
atatagaatt cggatccgga atagacattg tgtattacg                       39

<210> SEQ ID NO 34
<211> LENGTH: 31
<212> TYPE: DNA
<213> ORGANISM: Artificial Sequence
<220> FEATURE:
<223> OTHER INFORMATION: Synthetic oligonucleotide ADH2delflank2SpeIr

<400> SEQUENCE: 34
atataactag tagaggagag catagaaatg g                               31

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide loxP-kanMX-loxP SalIf

<400> SEQUENCE: 35
agctgaagct tcgtacgct                                             19

<210> SEQ ID NO 36

```
<211> LENGTH: 31
<212> TYPE: DNA
<213> ORGANISM: Artificial Sequence
<220> FEATURE:
<223> OTHER INFORMATION: Synthetic oligonucleotide loxP-kanMX-loxP
      EcoRIr

<400> SEQUENCE: 36
atatagaatt ccgcataggc cactagtgga t                                    31

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide pRS426XhoIcutFseq

<400> SEQUENCE: 37
gattaagttg ggtaacgcca                                                 20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide pRS426SpeIcutRseq

<400> SEQUENCE: 38
acagctatga ccatgattac                                                 20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide loxPKanMXloxPseqF

<400> SEQUENCE: 39
ctccttgaca gtcttgacgt                                                 20

<210> SEQ ID NO 40
<211> LENGTH: 39
<212> TYPE: DNA
<213> ORGANISM: Artificial Sequence
<220> FEATURE:
<223> OTHER INFORMATION: Synthetic oligonucleotide PgIflankKpnINotIf

<400> SEQUENCE: 40 ataggtac cgcggccgct tgctattgaa atgagcgtt                              39

<210> SEQ ID NO 41
<211> LENGTH: 37
<212> TYPE: DNA
<213> ORGANISM: Artificial Sequence
<220> FEATURE:
<223> OTHER INFORMATION: Synthetic oligonucleotide PgIflankEcoRISalIr

<400> SEQUENCE: 41
atatagaatt cgtcgacagg ctggtatctt gattcta                              37

<210> SEQ ID NO 42
<211> LENGTH: 37
<212> TYPE: DNA
<213> ORGANISM: Artificial Sequence
<220> FEATURE:
<223> OTHER INFORMATION: Synthetic oligonucleotide PgIflank2EcoRIBamHIf
```

<400> SEQUENCE: 42
atatagaatt cggatcctca aggaatggat gtgaaca                                    37

<210> SEQ ID NO 43
<211> LENGTH: 31
<212> TYPE: DNA
<213> ORGANISM: Artificial Sequence
<220> FEATURE:
<223> OTHER INFORMATION: Synthetic oligonucleotide PgIflank2SpeIr

<400> SEQUENCE: 43
atataactag tacaataaag tcttcacgac g                                          31

<210> SEQ ID NO 44
<211> LENGTH: 60
<212> TYPE: DNA
<213> ORGANISM: Artificial Sequence
<220> FEATURE:
<223> OTHER INFORMATION: Synthetic oligonucleotide Reg1delfwd

<400> SEQUENCE: 44
atgtcaacaa atctagcaaa ttacttcgcc ggtaagaaag ctgcaggtcg acaacccttta         60

<210> SEQ ID NO 45
<211> LENGTH: 63
<212> TYPE: DNA
<213> ORGANISM: Artificial Sequence
<220> FEATURE:
<223> OTHER INFORMATION: Synthetic oligonucleotide Reg1delrev

<400> SEQUENCE: 45
ctaactgctg tcatttccat tttcttgtgg cttgacgtca cactagtgga tctgatatca         60
cct                                                                         63

<210> SEQ ID NO 46
<211> LENGTH: 70
<212> TYPE: DNA
<213> ORGANISM: Artificial Sequence
<220> FEATURE:
<223> OTHER INFORMATION: Synthetic oligonucleotide KlMLS1

<400> SEQUENCE: 46
caatgaggct ttcttaagtt atgcaagctg tgtgtagagt cgtcatccct gcaggtcgac         60
aacccttaat                                                                  70

<210> SEQ ID NO 47
<211> LENGTH: 70
<212> TYPE: DNA
<213> ORGANISM: Artificial Sequence
<220> FEATURE:
<223> OTHER INFORMATION: Synthetic oligonucleotide KlMLS2

<400> SEQUENCE: 47
ggataaaagc tctatacaga ctactatcag aaaactttat taaagattca ggccactagt         60
ggatctgata                                                                  70

<210> SEQ ID NO 48
<211> LENGTH: 70
<212> TYPE: DNA
<213> ORGANISM: Artificial Sequence
<220> FEATURE:
<223> OTHER INFORMATION: Synthetic oligonucleotide KlIDP2F

<400> SEQUENCE: 48

```
gatactcaac gcagttaagc atctttagca atcaaattta gcagcccatt gcaggtcgac      60
aacccttaat                                                             70

<210> SEQ ID NO 49
<211> LENGTH: 70
<212> TYPE: DNA
<213> ORGANISM: Artificial Sequence
<220> FEATURE:
<223> OTHER INFORMATION: Synthetic oligonucleotide KlIDP2R

<400> SEQUENCE: 49
ggatatataa tgtagcagta aatcggatag ggaaaggcta gctttcttct ggccactagt      60
ggatctgata                                                             70

<210> SEQ ID NO 50
<211> LENGTH: 48
<212> TYPE: DNA
<213> ORGANISM: Artificial Sequence
<220> FEATURE:
<223> OTHER INFORMATION: Synthetic oligonucleotide KlCat8S661EHind

<400> SEQUENCE: 50
ggaagcttca ggtgtcctga agctgtacta ggtggtgatg gttccact                   48

<210> SEQ ID NO 51
<211> LENGTH: 33
<212> TYPE: DNA
<213> ORGANISM: Artificial Sequence
<220> FEATURE:
<223> OTHER INFORMATION: Synthetic oligonucleotide KlCat8revPst

<400> SEQUENCE: 51
aaactgcagc tcaattcttt ggtctccatt aag                                   33

<210> SEQ ID NO 52
<211> LENGTH: 66
<212> TYPE: DNA
<213> ORGANISM: Artificial Sequence
<220> FEATURE:
<223> OTHER INFORMATION: Synthetic oligonucleotide KlCat8S661Ef

<400> SEQUENCE: 52
cttcgtggaa aagttgtttc aatgtcacaa caactaaggt tacacaggtg tcctgaagct      60
gtacta                                                                 66

<210> SEQ ID NO 53
<211> LENGTH: 78
<212> TYPE: DNA
<213> ORGANISM: Artificial Sequence
<220> FEATURE:
<223> OTHER INFORMATION: Synthetic oligonucleotide KlCat8S661Er

<400> SEQUENCE: 53
cgtggaatgg tagagtttaa atcctcttgc ggctattgtt atctttatag gcctaaacta      60
gtggatctga tatcacct                                                    78

<210> SEQ ID NO 54
<211> LENGTH: 30
<212> TYPE: DNA
<213> ORGANISM: Artificial Sequence
<220> FEATURE:
<223> OTHER INFORMATION: Synthetic oligonucleotide BglIIgLYRfwd
```

<400> SEQUENCE: 54
atatagatct acaatggaag ttggtttctt					30

<210> SEQ ID NO 55
<211> LENGTH: 34
<212> TYPE: DNA
<213> ORGANISM: Artificial Sequence
<220> FEATURE:
<223> OTHER INFORMATION: Synthetic oligonucleotide BglIIgLYRrev

<400> SEQUENCE: 55
atatagatct ttactattct ctagagaatt taac					34

<210> SEQ ID NO 56
<211> LENGTH: 63
<212> TYPE: DNA
<213> ORGANISM: Artificial Sequence
<220> FEATURE:
<223> OTHER INFORMATION: Synthetic oligonucleotide IoMLSflank5fpRS

<400> SEQUENCE: 56
ggtatcgata agcttgatat cgaattcctg cagcccgggg ttgaataagc caattgcaca					60 tag					63

<210> SEQ ID NO 57
<211> LENGTH: 60
<212> TYPE: DNA
<213> ORGANISM: Artificial Sequence
<220> FEATURE:
<223> OTHER INFORMATION: Synthetic oligonucleotide IoMLSflank5rIopPGK

<400> SEQUENCE: 57
gtgtaaacgt ggacattgat gttgccgttg cagcaaggat gtgaagtcaa tcttgtccct					60

<210> SEQ ID NO 58
<211> LENGTH: 60
<212> TYPE: DNA
<213> ORGANISM: Artificial Sequence
<220> FEATURE:
<223> OTHER INFORMATION: Synthetic oligonucleotide IoMLSflank3floxP

<400> SEQUENCE: 58
tatacgaagt tattaggtga tatcgactag tggcctatgc aagggaagct gggatttctc					60

<210> SEQ ID NO 59
<211> LENGTH: 66
<212> TYPE: DNA
<213> ORGANISM: Artificial Sequence
<220> FEATURE:
<223> OTHER INFORMATION: Synthetic oligonucleotide IoMLSflank3rpRS

<400> SEQUENCE: 59
agctggagct ccaccgcggt ggcggccgct ctagaactag cccgggaccc aaatccaagg					60 ttcaga					66

<210> SEQ ID NO 60
<211> LENGTH: 26
<212> TYPE: DNA
<213> ORGANISM: Artificial Sequence
<220> FEATURE:
<223> OTHER INFORMATION: Synthetic oligonucleotide AnMLS-5'-For

<400> SEQUENCE: 60
gaattccagc ggaagttaga gttgac					26

<210> SEQ ID NO 61
<211> LENGTH: 27
<212> TYPE: DNA
<213> ORGANISM: Artificial Sequence
<220> FEATURE:
<223> OTHER INFORMATION: Synthetic oligonucleotide AnMLS-5'-Rev

<400> SEQUENCE: 61 cccggggca ttgtggtaga agtacag                27

<210> SEQ ID NO 62
<211> LENGTH: 28
<212> TYPE: DNA
<213> ORGANISM: Artificial Sequence
<220> FEATURE:
<223> OTHER INFORMATION: Synthetic oligonucleotide AnMLS-3'-For

<400> SEQUENCE: 62
cccgggcgat gctaataaac ttgtaggg              28

<210> SEQ ID NO 63
<211> LENGTH: 26
<212> TYPE: DNA
<213> ORGANISM: Artificial Sequence
<220> FEATURE:
<223> OTHER INFORMATION: Synthetic oligonucleotide AnMLS-3'-Rev

<400> SEQUENCE: 63
gaattcgatg cggagtatgg atttgg                26

<210> SEQ ID NO 64
<211> LENGTH: 30
<212> TYPE: DNA
<213> ORGANISM: Artificial Sequence
<220> FEATURE:
<223> OTHER INFORMATION: Synthetic oligonucleotide pyrG-del-Fn

<400> SEQUENCE: 64
tatacccggg tgattgaggt gattggcgat            30

<210> SEQ ID NO 65
<211> LENGTH: 28
<212> TYPE: DNA
<213> ORGANISM: Artificial Sequence
<220> FEATURE:
<223> OTHER INFORMATION: Synthetic oligonucleotide pyrG-del-Rn

<400> SEQUENCE: 65
tatacccggg ttatcacgcg acggacat              28

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide AnMLS-screen-for

<400> SEQUENCE: 66
ctaacaacag acagattcca                       20

<210> SEQ ID NO 67
<211> LENGTH: 22
<212> TYPE: DNA
<213> ORGANISM: Artificial Sequence
<220> FEATURE:

<223> OTHER INFORMATION: Synthetic oligonucleotide AnMLS-screen-rev

<400> SEQUENCE: 67
cctccctaca agtttattag ca                                         22

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide AnglyrScreenFor

<400> SEQUENCE: 68
ggctatgtct atgaatctcc                                            20

<210> SEQ ID NO 69
<211> LENGTH: 18
<212> TYPE: DNA
<213> ORGANISM: Artificial Sequence
<220> FEATURE:
<223> OTHER INFORMATION: Synthetic oligonucleotide AnglyrScreenRev

<400> SEQUENCE: 69
ctggcttctt actccctg                                              18

<210> SEQ ID NO 70
<211> LENGTH: 1017
<212> TYPE: DNA
<213> ORGANISM: Thermus thermophilus

<400> SEQUENCE: 70
atgcggccta cgggagcccc accgtggcgg tggccgagct ctccttcgcc ggggcgtaac    60
cccaccccgg tcaaaagagg catgaaggtc ttcgtcaccc gcacccttcc cgggaaggcc   120
ctggaccgcc tgcgggaaag gggcctcgag gtggaggtcc accgggggct cttcctcccc   180
aaagcggaac tcctaaagcg ggtggagggg cggtgggcc tcatccccac ggtggaggac    240
cgcatagacg ccgaggtgat ggaccgggcc aagggcctca aggtcatcgc tgctacagc    300
gtggggggtgg accacgtgga cctcgaggcg cccggggaga ggggcatccg ggtcacgcac   360
accccccggggg tcctcaccga ggccaccgcc gacctcaccc tcgccctcct cctcgccgtg   420
gcgaggcggt tggtggaggg gcggcctac gcccgggacg ggctctggag ggcctggcac    480
cccgagctcc tcctgggcct ggacctccag ggcttgaccc tgggcctcgt gggcatgggg    540
cggatcggcc aggcggtggc caagagggcc ctggccttcg ggatgcgggt ggtctaccac    600
gcccgcaccc ccaagcccct cccctacccc ttcctctccc tggaggagct ccttaaagag    660
gcggacgtcg tctccctcca caccccctc acccgaaa cccacaggct cctcaaccgg    720
gaaaggctct tcgccatgaa gcggggcgcc atcctcatca acccgcccg ggggccctg    780
gtggacaccg aggccctggt ggaggcctta aggggccacc tcttcggggc gggcctggac   840
gtgaccgacc ccgagcccct gccccaggac caccccctct accgcctccc caacgccgtc   900
attccccccc acatcggctc ggcggggaga acgacccggg agcgcatggc ggaggtggcg   960
gtggagaacc tcctcgccgt cctggagggg agggagccgc caacccggt agtatag       1017

<210> SEQ ID NO 71
<211> LENGTH: 338
<212> TYPE: PRT
<213> ORGANISM: Thermus thermophilus

<400> SEQUENCE: 71

Met Arg Pro Thr Gly Ala Pro Pro Trp Arg Trp Pro Ser Ser Pro Ser
1               5                   10                  15

Pro Gly Arg Asn Pro Thr Pro Val Lys Arg Gly Met Lys Val Phe Val
            20                  25                  30

Thr Arg Thr Leu Pro Gly Lys Ala Leu Asp Arg Leu Arg Glu Arg Gly
        35                  40                  45

Leu Glu Val Glu Val His Arg Gly Leu Phe Leu Pro Lys Ala Glu Leu
    50                  55                  60

Leu Lys Arg Val Glu Gly Ala Val Gly Leu Ile Pro Thr Val Glu Asp
65                  70                  75                  80

Arg Ile Asp Ala Glu Val Met Asp Arg Ala Lys Gly Leu Lys Val Ile
                85                  90                  95

Ala Cys Tyr Ser Val Gly Val Asp His Val Asp Leu Glu Ala Ala Arg
            100                 105                 110

Glu Arg Gly Ile Arg Val Thr His Thr Pro Gly Val Leu Thr Glu Ala
            115                 120                 125

Thr Ala Asp Leu Thr Leu Ala Leu Leu Leu Ala Val Ala Arg Arg Val
    130                 135                 140

Val Glu Gly Ala Ala Tyr Ala Arg Asp Gly Leu Trp Arg Ala Trp His
145                 150                 155                 160

Pro Glu Leu Leu Leu Gly Leu Asp Leu Gln Gly Leu Thr Leu Gly Leu
                165                 170                 175

Val Gly Met Gly Arg Ile Gly Gln Ala Val Ala Lys Arg Ala Leu Ala
            180                 185                 190

Phe Gly Met Arg Val Val Tyr His Ala Arg Thr Pro Lys Pro Leu Pro
        195                 200                 205

Tyr Pro Phe Leu Ser Leu Glu Glu Leu Leu Lys Glu Ala Asp Val Val
    210                 215                 220

Ser Leu His Thr Pro Leu Thr Pro Glu Thr His Arg Leu Leu Asn Arg
225                 230                 235                 240

Glu Arg Leu Phe Ala Met Lys Arg Gly Ala Ile Leu Ile Asn Thr Ala
                245                 250                 255

Arg Gly Ala Leu Val Asp Thr Glu Ala Leu Val Glu Ala Leu Arg Gly
            260                 265                 270

His Leu Phe Gly Ala Gly Leu Asp Val Thr Asp Pro Glu Pro Leu Pro
        275                 280                 285

Gln Asp His Pro Leu Tyr Arg Leu Pro Asn Ala Val Ile Thr Pro His
    290                 295                 300

Ile Gly Ser Ala Gly Arg Thr Thr Arg Glu Arg Met Ala Glu Val Ala
305                 310                 315                 320

Val Glu Asn Leu Leu Ala Val Leu Glu Gly Arg Glu Pro Pro Asn Pro
                325                 330                 335

Val Val

<210> SEQ ID NO 72
<211> LENGTH: 568
<212> TYPE: PRT
<213> ORGANISM: candida krusei

<400> SEQUENCE: 72

Met Thr Lys Pro Ala Glu Leu Tyr Cys Thr Ser Leu Glu Gly Val Gln
1               5                   10                  15

Val Val Gly Glu Val Ser Asp Lys Pro Leu Leu Ser Glu Ala Thr Pro
            20                  25                  30

-continued

Arg Asp Ile Leu Thr Ile Asp Ala Leu Lys Phe Val Leu Leu His
            35                  40                  45

Arg Ala Phe Asn Gly Thr Arg Lys Gln Leu Leu Ala Asn Arg Gln Asp
 50                  55                  60

Val Gln Lys Arg Leu Asp Ala Gly Glu Ser Leu Thr Phe Leu Lys Glu
 65                  70                  75                  80

Thr Glu Tyr Ile Arg Asn Asp Pro Asn Trp Arg Cys Ala Thr Asn His
                     85                  90                  95

Pro Lys Leu Met Cys Arg Lys Val Glu Ile Thr Gly Pro Pro Asp Ala
                 100                 105                 110

Lys Met Ile Ile Asn Ala Phe Asn Thr Asn Val His Thr Tyr Met Thr
                 115                 120                 125

Asp Phe Glu Asp Ser Cys Ala Pro Thr Trp Ser Asn Met Leu Tyr Gly
             130                 135                 140

Gln Val Asn Leu Tyr Asp Ala Ile Arg Asp Lys Ile Asp Phe Thr Asn
145                 150                 155                 160

Asp Lys Thr Gly Lys Arg Tyr Lys Ile Asn Arg Glu Gly Arg Arg Val
                 165                 170                 175

Pro Val Met Ile Val Arg Pro Arg Gly Trp His Met Val Asp Gln His
                 180                 185                 190

Ile Leu Val Asp Gly Glu Pro Ile Ser Ala Ser Ile Leu Asp Phe Gly
                 195                 200                 205

Leu Phe Phe Tyr His Asn Ala Lys Tyr Leu Ile Ser Gln Gly Leu Gly
             210                 215                 220

Pro Phe Phe Tyr Leu Pro Lys Met Glu His Trp Lys Glu Ala Lys Leu
225                 230                 235                 240

Trp Asn Asp Ile Phe Cys Val Ala Gln Asp Cys Leu Glu Ile Pro Arg
                 245                 250                 255

Gly Thr Ile Lys Ala Thr Val Leu Ile Glu Thr Leu Pro Ile Ser Tyr
                 260                 265                 270

Gln Leu Asp Glu Val Leu Tyr Ala Leu Lys Asp His Ser Ser Gly Leu
             275                 280                 285

Asn Cys Gly Arg Trp Asp Tyr Met Phe Ser Thr Ile Lys Arg Leu Arg
             290                 295                 300

Asn Gln Lys Asp Lys Ile Leu Pro Asp Arg Gln Gln Val Thr Met Thr
305                 310                 315                 320

Val Pro Phe Met Thr Asn Tyr Val Lys Gln Leu Ile Lys Val Cys His
                 325                 330                 335

Lys Arg Gly Val His Ala Met Gly Gly Met Ala Ala Phe Ile Pro Ile
             340                 345                 350

Lys Asn Asp Glu Glu Ala Asn Lys Val Ala Leu Glu Ala Val Arg Lys
             355                 360                 365

Asp Lys Leu Arg Glu Val Leu Ala Gly His Asp Gly Thr Trp Ile Ala
 370                 375                 380

His Pro Gly Leu Leu Asp Thr Ala Leu Ser Val Phe Glu Glu His Met
385                 390                 395                 400

Pro Thr Pro Asn Gln Leu Tyr Lys Leu Lys Asp Asp Val Ser Val Thr
                 405                 410                 415

Glu Ser Asp Leu Val Asp Thr Asn Ile Glu Gly Gly Gln Ile Thr Met
             420                 425                 430

Lys Gly Leu Asn Ala Asn Ile Tyr Ile Gly Leu Asn Tyr Met Glu Ser
             435                 440                 445

Trp Leu Arg Gly Leu Gly Cys Val Pro Ile Asn His Leu Met Glu Asp
            450                 455                 460

Ala Ala Thr Ala Glu Val Ser Arg Leu Gln Leu Trp Ser Trp Cys Lys
465                 470                 475                 480

His Gln Val Lys Met Asn Asp Thr Gly Lys Thr Ile Thr Pro Asp Phe
                485                 490                 495

Val Cys Gln Leu Ile Asp Glu Glu Val Ala Arg Cys Ser His Lys Glu
                500                 505                 510

Gly Asn Lys Tyr Glu Leu Ala Ala Gln Cys Leu Lys Asp Glu Ile Ser
            515                 520                 525

Gly Lys Lys Pro Val Ala Glu Phe Leu Thr Asp Ile Leu Tyr Pro Tyr
        530                 535                 540

Ile Ala Thr Pro Gly Lys Pro Val Asp Leu Asn Ser Leu Lys Gln Ser
545                 550                 555                 560

Thr Pro Val Cys Ala Ser Arg Leu
                565

<210> SEQ ID NO 73
<211> LENGTH: 61
<212> TYPE: DNA
<213> ORGANISM: Artificial Sequence
<220> FEATURE:
<223> OTHER INFORMATION: Synthetic oligonucleotide IoMLSflank5fpRS2

<400> SEQUENCE: 73
ggtatcgata agcttgatat cgaattcctg cagcccgggg cttccacatg gtttcttctt    60
g                                                                   61

<210> SEQ ID NO 74
<211> LENGTH: 60
<212> TYPE: DNA
<213> ORGANISM: Artificial Sequence
<220> FEATURE:
<223> OTHER INFORMATION: Synthetic oligonucleotide IoMLSflank5rIopPGK2

<400> SEQUENCE: 74
gtgtaaacgt ggacattgat gttgccgttg cagcaaggat tgtgcaattg gcttattcaa    60

<210> SEQ ID NO 75
<211> LENGTH: 60
<212> TYPE: DNA
<213> ORGANISM: Artificial Sequence
<220> FEATURE:
<223> OTHER INFORMATION: Synthetic oligonucleotide IoMLSflank3floxP2

<400> SEQUENCE: 75
tatacgaagt tattaggtga tatcgactag tggcctatgc actcctgttt gtgcatcaag    60

<210> SEQ ID NO 76
<211> LENGTH: 66
<212> TYPE: DNA
<213> ORGANISM: Artificial Sequence
<220> FEATURE:
<223> OTHER INFORMATION: Synthetic oligonucleotide IoMLSflank3rpRS

<400> SEQUENCE: 76
agctggagct ccaccgcggt ggcggccgct ctagaactag cccgggaatt taaacgtgca    60
agtggc                                                              66

<210> SEQ ID NO 77
<211> LENGTH: 32

```
<212> TYPE: DNA
<213> ORGANISM: Artificial Sequence
<220> FEATURE:
<223> OTHER INFORMATION: Synthetic oligonucleotide 221MLS3fSalI

<400> SEQUENCE: 77
atatatgtcg acactcctgt ttgtgcatca ag                                  32

<210> SEQ ID NO 78
<211> LENGTH: 32
<212> TYPE: DNA
<213> ORGANISM: Artificial Sequence
<220> FEATURE:
<223> OTHER INFORMATION: Synthetic oligonucleotide 222MLS3rSalI

<400> SEQUENCE: 78
atatatgtcg acaatttaaa cgtgcaagtg gc                                  32

<210> SEQ ID NO 79
<211> LENGTH: 33
<212> TYPE: DNA
<213> ORGANISM: Artificial Sequence
<220> FEATURE:
<223> OTHER INFORMATION: Synthetic oligonucleotide 223MLS5fSpeI

<400> SEQUENCE: 79
atatatacta gtcttccaca tggtttcttc ttg                                 33

<210> SEQ ID NO 80
<211> LENGTH: 38
<212> TYPE: DNA
<213> ORGANISM: Artificial Sequence
<220> FEATURE:
<223> OTHER INFORMATION: Synthetic oligonucleotide 224MLS5rSpeIBamHI

<400> SEQUENCE: 80
atatatacta gtggatcctg tgcaattggc ttattcaa                            38

<210> SEQ ID NO 81
<211> LENGTH: 71
<212> TYPE: DNA
<213> ORGANISM: Artificial Sequence
<220> FEATURE:
<223> OTHER INFORMATION: Synthetic oligonucleotide 234KlMLSflankTPIF

<400> SEQUENCE: 81
caatgaggct ttcttaagtt atgcaagctg tgtgtagagt cgtcatccct ggatctacgt    60
atggtcattt c                                                        71

<210> SEQ ID NO 82
<211> LENGTH: 70
<212> TYPE: DNA
<213> ORGANISM: Artificial Sequence
<220> FEATURE:
<223> OTHER INFORMATION: Synthetic oligonucleotide 235KlMLSflankURAR

<400> SEQUENCE: 82
ggataaaagc tctatacaga ctactatcag aaaactttat taaagattca ccctatgcgg    60
tgtgaaatac                                                          70

<210> SEQ ID NO 83
<211> LENGTH: 82
<212> TYPE: DNA
<213> ORGANISM: Artificial Sequence
<220> FEATURE:
```

```
<223> OTHER INFORMATION: Synthetic oligonucleotide 236KlMLSURaflankLEUf

<400> SEQUENCE: 83
atatgcggcc gcgtctagct ccaattcgcc ctatagtgag tcgtattaca attcactggc        60
cgctgaagct tcgtacgctg ca                                                  82

<210> SEQ ID NO 84
<211> LENGTH: 83
<212> TYPE: DNA
<213> ORGANISM: Artificial Sequence
<220> FEATURE:
<223> OTHER INFORMATION: Synthetic oligonucleotide 237KlMLSflankLEUr

<400> SEQUENCE: 84
atatgcggcc gcggataaaa gctctataca gactactatc agaaactttt attaaagatt        60
caataggcca ctagtggatc tga                                                 83
```

EUKARYOTIC CELL AND METHOD FOR PRODUCING GLYCOLIC ACID

FIELD OF THE INVENTION

This invention relates to a eukaryotic host and a method for producing glycolic acid using eukaryotic host cells, especially cells of a genetically modified fungal host. Further this invention relates to glycolic acid obtained using the method described here and the use of eukaryotic cells in production of glycolic acid.

The sequence listing named VTT328US_2014-04-01_Sequence_listing.txt, which was created on 2012-10-04 and is 34 kilobytes, is herein incorporated by reference in its entirety.

DESCRIPTION OF RELATED ART

Glycolic acid is a widely used chemical. It has applications within cosmetic field and organic synthesis of polyglycolic acid and other biocompatible polymers. In textile industry it is used as a dyeing and tanning agent and in food processing as a flavouring agent and as a preservative. Traditionally glycolic acid is usually derived from fossil fuels but it is possible to derive glycolic acid from biomass by using metabolically engineered *E. coli*.

Glycolic acid is the smallest α-hydroxy acid and it is not naturally produced by microorganisms at least in feasible quantities. This is different to lactic acid which is also a small α-hydroxy acid, but this acid is produced naturally by a large number of microorganisms. To produce glycolic acid from carbohydrates in a fermentative way using microorganisms requires genetically engineered microorganisms. Previously *Escherichia coli* strains were described that were engineered to produce glycolic acid from glucose (WO 2007/141316 A2, WO2010/108909 A1 and WO2011/036213). In these strains the glyoxylate cycle was disrupted by deleting the malate synthase and overexpressing an endogenous glyoxylate reductase so that the glyoxylate produced by the isocitrate lyase could be converted to glycolic acid. Also other modifications were done to channel more carbon to the glyoxylate cycle or to prevent the utilization of glyoxylic acid. *E. coli* strains engineered in this way were producing glycolic acid from glucose.

A characteristic of *E. coli* and bacteria in general is that the inner space of the cell or the cytosol of the organism is not compartmentalized. This is different in eukaryotic organisms. Eukaryotic cells, including yeast and filamentous fungal cells, have different compartments that are separated by membranes, such as vacuoles, mitochondria or peroxisomes. In difference to bacteria the cellular reactions take place in different compartments. For example the reactions of the TCA cycle (Krebs cycle, citric acid cycle) are located in the mitochondria, whereas the different reactions of the glyoxylate cycle are in separate compartments. According to current understanding isocitrate lyase and malate synthase are peroxisomal in filamentous fungi. In yeasts such as *S. cerevisiae* isocitrate lyase and malate synthase are cytosolic. The citrate synthase is located in the peroxisomes and in the mitochondria, the aconitase can be in mitochondria and cytosol and the succinate dehydrogenase is exclusively in mitochondria. The distribution of the enzyme activities to different compartments and inability of the metabolites to freely travel between the compartments makes a fundamental difference to metabolic pathways and consequently the approaches to engineer these pathways by means of genetic engineering are essentially different. It is therefore not clear whether the teaching disclosed in the WO2007/141316 A2, WO2010/108909 A1 and WO2011/036213 can be applied to eukaryotic microorganism.

Using *E. coli* for the production of glycolic acid has several drawbacks. *E. coli* is requiring a complex growth medium which is in general more expensive than growth media for yeast or filamentous fungi. Another drawback is that *E. coli* is operating close to neutral pH. This increases the contamination risk and in the case of acid production it requires base to neutralize the acid. Further, in neutral conditions the produced glycolic acid is in dissociated form, which is a disadvantage in downstream processing.

OBJECTS AND SUMMARY OF THE INVENTION

It is an aim of the invention to provide a eukaryotic host organism and a method for producing glycolic acid using said host. Particularly, the aim is to provide a production host and a method that allows using mildly acidic or acidic conditions.

These and other objects are achieved by the present invention as hereinafter described and claimed. The first aspect of the invention is a eukaryotic production host. Characteristic to said host is that it is genetically modified to express glyoxylate reductase gene and produce glycolic acid.

The second aspect of the invention is a method for producing glycolic acid. According to the invention the method comprises the steps of culturing a eukaryotic host encoding glyoxylate reductase activity and optionally recovering the glycolic acid from said medium.

The third aspect of the invention is a product obtained by culturing the production host of the invention or by using the method of the invention.

The fourth aspect of the invention is the use of eukaryotic host in production of glycolic acid.

Some of the embodiments of the invention are disclosed in the dependent claims.

DESCRIPTION OF THE PREFERRED EMBODIMENTS OF THE INVENTION

Figure 18:
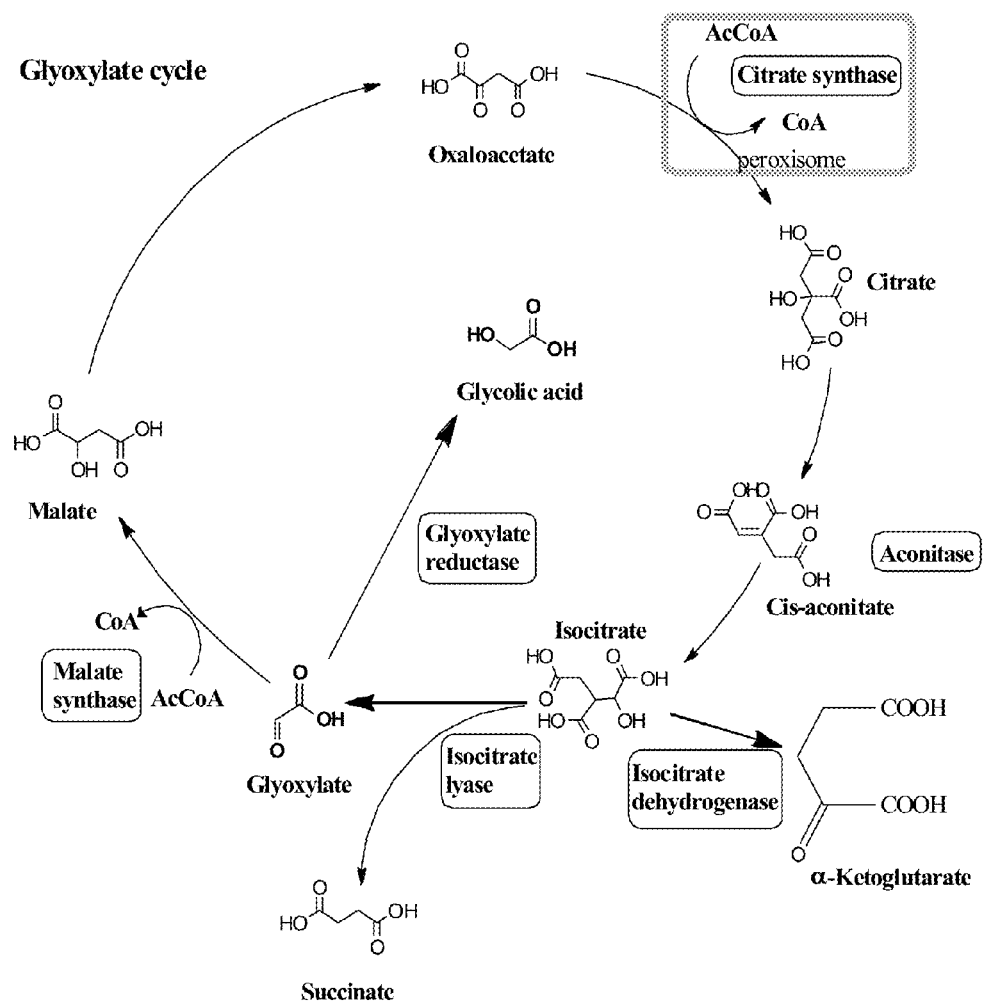
FIG. 18. is the schematic representation of the metabolic route leading to glycolic acid production.

This invention relates to a eukaryotic host which is genetically modified to express glyoxylate reductase gene and produce glycolic acid. The metabolic route leading to glycolic acid production is illustrated as FIG. 18.

The eukaryotic host may be any eukaryotic organism but most usually it is a cell, preferably a micro-organism. In one embodiment the cell is a fungal cell. When compared to e.g. *E. coli* fungal cells are generally more tolerant to changing culture conditions such as low pH, lignocellulosic hydrolysates, impurities, degradation products of hydrolytic enzymes and toxins. They also have lower nutritional requirements compared to bacteria most commonly used in industrial processes. Thus fungal production is an economic approach to microbial production of glycolic acid.

In one embodiment the host is a yeast cell. Yeasts like *Saccharomyces cerevisiae* or filamentous fungi like *Aspergillus niger* are naturally operating at very acidic pH. Yeast produced in fermentations is often used as cattle feed which benefits the economics of the process. Bacteria are generally not used as cattle feed but deemed a waste.

Suitable yeasts are for example the genera *Saccharomyces, Kluyveromyces, Candida, Scheffersomyces, Pachysolen* and *Hansenula*. Yeast species of particular interest include *S. cerevisiae, S. exiguus, K. marxianus, K. lactis, K. thermotolerans, C. sonorensis, C. krusei* (also known as *Issachenkia orientalis* and *Pichia kudriavzevii*), *C. shehatae, Pachysolen tannophilus* and *Scheffersomyces stipitis*.

In one embodiment the host is a filamentous fungus. One particular advantage of using filamentous fungi to produce glycolic acid is that it can be done in a consolidated process, meaning that the fungus produces the enzymes for biomass hydrolysis and ferments the resulting sugars in the same process.

Suitable filamentous fungi hosts are for example of the genera *Aspergillus, Trichoderma, Monascus*, and *Penicillium*. Fungal species of particular interest include *A. niger, A. ficuum, A. phoenicis, T. reesei, T. harzianum, M. ruber*, and *P. chrysogenum*. Filamentous fungi allow using only partially hydrolysed biomass as a carbon source which is benefit if some lignocellulosic waste is used as a carbon source. *A. niger* is also a well known citric acid producer and by metabolic engineering it can be made an efficient host for glycolic acid production.

In a preferred embodiment the host includes those of the species *S. cerevisiae, S. exiguus, K. marxianus, K. lactis, C. krusei* and *A. niger*.

The host organism of this invention is genetically modified and may contain also other genetic modifications than those specifically described herein. Methods for making modifications of these types are generally well known and are described in various practical manuals describing laboratory molecular techniques.

A phrase "genetically modified to express" as used herein covers the cells where a protein-encoding polynucleotide has been transformed in such a manner that the host is capable of producing an active protein or where a promoter region of a cell has been modified to allow or enhance the expression of a heterologous or homologous gene encoding glyoxylate reductase activity.

In one embodiment of the invention the host is capable of producing glycolic acid at pH below 6, preferably below 5.5, below 5.0, below 4.5, below 4.0, below 3.5, below 3.0, below 2.5 and even below 2.0, until pH 1.5. Acidic or mildly acidic culture conditions reduce risk of contaminations and thus improve the process hygiene and safety. Each contaminated large scale fermentation results in direct loss of money. For the downstream processing it is of advantage when the glycolic acid is produced at acidic pH. Glycolic acid has a pKa of 3.83 meaning that below a pH 3.8 it is mainly in the acid form which facilitates the separation.

In one embodiment of the invention the host is capable of producing glycolic acid in non-buffered culturing conditions. In other words the strain is tolerant to decreasing pH during the cultivation process. This simplifies the culturing process and thereby reduces costs. However, this characteristic naturally does not exclude possibility to regulate the pH conditions using bases (or acids) or even buffering agents.

In one embodiment the glyoxylate reductase gene is a heterologous gene to a host. Especially when the Km value of the homologous gene is high it is beneficial to replace the gene by heterologous gene having lower Km value. The heterologous gene is preferably obtained from a plant source, gene obtained from *Arabidopsis thaliana* (Hoover et al. 2007) being the most preferred. It is also possible to use endogenous or native genes for production and modify the cell to overproduce glyoxylate reductase.

In one embodiment the glyoxylate reductase enzyme is characterized by having an EC number EC 1.1.1.79 (NADP+) or EC 1.1.1.26 (NAD+). Enzymes of class EC 1.1.1.79 (glyoxylate:NADP+ reductases, CAS 37250-17-2) catalyze reduction of glyoxylate using NADPH into glycolic acid and NADP or reduces hydroxypyruvate to glycerate. *A. thaliana* glyoxylate reductase designated here as "GLYR1" is one example of this class. Enzymes of class EC 1.1.1.26 (glyoxylate:NAD+ reductases, CAS 9028-32-4) reduces glyoxylate to glycolic acid or hydroxypyruvate to D-glycerate. In the European chemical legislation the enzymes are defined according to the type of reaction they catalyze. Each enzyme is given a systematic name and an IUBMB (International Union of Biochemistry and Molecular Biology) number such as EC 1.1.1.26.

It is known that different enzymes can have the same enzyme activity but have very different amino acid sequences. The Glyr 1 from *Arabidopsis thaliana* (GenBank accession number AY044183, EC 1.1.1.79) and the glyoxylate reductase from *Thermus thermophilus* HB27 (Gene identifier TT_C0431, Protein ID AAS80779.1) Biotechnology Progress (2008) 24 (2) 321-325 are examples for this. Both enzymes show glyoxylate reductase activity when heterologously expressed but when the amino acid sequences are aligned in a CLUSTALW2sequence alignment the identities are only 12%. Comparison of the identity percentages of different glyoxylate reductases is presented in Table 1.

TABLE 1

Comparison of different glyoxylate reductase protein sequences done with ClustalW2 alignment (Cost matrix: BLOSUM, Gap open cost 10, Gap extend cost 0, 1)

| Glyoxylate reductase protein from | Identity-% with *A. thaliana* Glyr1 (SEQ ID NO: 3) |
|---|---|
| *Arabidopsis thaliana* (GR2) | 48% |
| *Escherichia coli* (ycdW) | 14% |
| *Homo sapiens* | 13% |
| *Pyrococcus horikoshii* | 14% |
| *Thermus thermophilus* HB27 | 12% |
| *Thermococcus litoralis* | 11% |
| *Rhizobium etli* (GrxA) | 12% |
| *Saccharomyces cerevisiae* (GOR1) | 13% |

In one embodiment the host cell comprises the genes encoding proteins characterized by SEQ ID NO: 3, or SEQ ID NO: 71 or a sequence having at least 40%, 50%, 55%, 60% or identity, preferably at least 65%, 70%, 75% or 80% identity, 85% identity, more preferably at least 90% identity and most preferably at least 95% or even 98% identity to gene encoding the polypeptide having SEQ ID NO: 3 or SEQ ID NO: 71, or an active fragment thereof. In preferred embodiment the encoded enzymes has characteristics of SEQ ID NO: 3.

As used in the present context the term "identity" refers to the global identity between two amino acid sequences compared to each other from the first amino acid encoded by the corresponding gene to the last amino acid. For the purposes of the present invention identity is preferably determined by means of known computer programs using standard algorithms. An example of such a program is NCBI BLAST; BLASTp (comparison of known protein sequences, amino acids), BLASTn (comparison of nucleic acid sequences), BLASTx (comparison of translated nucleic acid sequences against know protein sequences).

"An active fragment" means a fragment having all the parts needed for completing the function typical for the protein.

It is understood by the skilled reader that the gene must be operably linked to the sequences regulating the expression of the gene. Two DNA sequences are operably linked when the function of the promoter results in transcription. An operable linkage is a linkage in which a sequence is connected to a regulatory sequence (or sequences) in such a way as to place expression of the sequence under the influence or control of the regulatory sequence.

In one embodiment the gene is genetically optimized. It is understood by a skilled man that heterologous gene obtained by a different organism may need genetic optimization in order to properly function in the host cell. In one embodiment the heterologous gene is genetically optimized to fit the host systems.

Standard molecular biology methods can be used in the cloning of glyoxylate reductase or other overexpressed genes. The basic methods used like isolation and enzyme treatments of DNA, *E. coli* transformations made for plasmid constructions, the isolation of the vectors or fragments containing the said gene and amplification of fragments by PCR are described in the standard molecular biology handbooks e.g. Sambrook et al. (1989) and Sambrook and Russell (2001). Genetic modification of the host fungus is accomplished in one or more steps via the design and construction of appropriate vectors and transformation of the host fungus with those vectors. Electroporation, protoplast-PEG and/or chemical (such as calcium chloride- or lithium acetate-based) transformation methods can be used.

The heterologous gene can be stably introduced into the genome of the host cell. Stable transformation is obtained when the expression cassette is integrated to the chromosomal DNA of the host. Targeted integration can be accomplished by designing a vector having regions that are homologous to the upstream (5'-) and downstream (3'-) flanks of the target gene. Either or both of these regions may include a portion of the coding region of the target gene. The GLYR1 cassette (including suitable promoters and terminators if different from those of the target gene) and/or selection markers (with suitable promoters and terminators) will reside between the regions that are homologous to the upstream and downstream flanks of the target gene. Stable transformation is preferred as no selection pressure is needed during cultivation but alternatively also episomal plasmids and other non-integrated constructs are within this invention.

The use of native (homologous to the host cell) or non-native (heterologous to the host cell) promoters and terminators, together with respective upstream and downstream flanking regions, can permit the targeted integration of the GLYR1 or any other gene mentioned above, or any other gene further described below, into specific loci of the host cell's genome, and for simultaneous integration of the said gene and deletion of a native gene, such as, for example, a malate synthase (e.g. MLS1 or DAL7) encoding gene.

The exogenous glyoxylate reductase gene may be maintained on a self-replicating plasmid, integrated randomly into the host cell's genome or inserted at one or more targeted locations. Examples of targeted locations include the locus of a gene that is desirably deleted or disrupted, such as the MLS1 gene in *S. cerevisiae* or the malate synthase gene in *A. niger*.

In one embodiment the cell has been further modified to overexpress the gene encoding glyoxylate reductase.

The overexpressed genes—such as glyoxylate reductase (e.g. GLYR1 gene from *A. thaliana*), isocitrate lyase, aconitase, citrate synthase, fumarate reductase, acetyl-coenzyme A synthetase or a gene regulating glyoxylate cycle is under the control of a promoter and a terminator, both of which are functional in the modified fungal cell. As used herein, the term "promoter" refers to a sequence located upstream (e.g., 5') to the translation start codon of a structural gene and which controls the start of transcription of the structural gene. Similarly, the term "terminator" refers to a sequence located downstream (e.g., 3') to the translation stop codon of a structural gene and which controls the termination of transcription of the structural gene. A promoter or terminator is "operatively linked" to a structural gene if its position in the genome relative to that of the structural gene is such that the promoter or terminator, as the case may be, performs its transcriptional control function.

The genetically modified fungus may contain a single copy or multiple copies of the glyoxylate reductase gene (e.g. GLYR1 gene) or any other gene mentioned above, or any other gene further described below. If multiple copies of the glyoxylate reductase gene are present, from 2 to 10 or more copies may be integrated into the genome, or >100 copies may be present on self-replicating plasmids. If multiple copies of the glyoxylate reductase gene are integrated into the genome, they may be integrated at a single locus (so they are adjacent each other), or at several loci within the host's genome. It is possible for different glyoxylate reductase genes to be under the control of different types of promoters and/or terminators.

In one embodiment the production host has been further modified by increasing the flux towards the glyoxylate cycle. The flux towards the cycle can be increased e.g. by overexpressing isocitrate lyase, aconitase, citrate synthase or fumarate reductase. Heterologous fumarate reductase would convert succinate into fumarate, which can be then metabolized further and used again in the glyoxylate cycle. Increase of the glyoxylate flux may require also reducing activity of the enzymes consuming the intermediates of the cycle, e.g. attenuating expression of malate synthase(s), NAD and/or NADP dependent mitochondrial and/or cytosolic isocitrate dehydrogenase(s). Increase of flux towards the cycle results in more efficient production of glycolic acid.

In this connection term attenuating refers to partial or total deletion or knock-out of the said gene, modification of regulatory regions of the said gene in order to decrease its activity or silencing or decreasing the activity of the said gene by any methods without restricting to those mentioned above.

The yield of the glycolic acid can be increased by several ways. Increased yield saves the fermentation costs and enhances the down-stream processing.

In one embodiment the production host has been further modified by modifying the genes regulating the glyoxylate cycle i.e. genes involved in negative regulation of glucoserepressible genes. This can be done for example by activating genes such as CAT8 in *S. cerevisiae* or in *K. lactis* by mutation or overexpression or by attenuating genes such as REG1 in *S. cerevisiae*.

In one embodiment the production host has been further modified by improving NADPH availability. This can be done e.g. by overexpressing cytosolic aldehyde dehydrogenase such as ALD6 in *S. cerevisiae* or deleting phosphoglucose isomerase gene such as PGI1 in *S. cerevisiae* or *K. lactis*. Glyoxylate reductases are usually NADPH dependent and thus need NADPH for functioning. Glyoxylate reductase can be also NADH dependent and in these cases the improvement of NADPH availability is unnecessary.

In one embodiment, the production host has been further modified to control ethanol production and utilization.

Thus, in one embodiment the cell has been further modified by attenuating genes involved in alcohol production in yeast or production of hydrolytic enzymes in filamentous fungi. Alcohol production competes with the glyoxylate cycle and it can be preferred to decrease it. This can be done e.g. by overexpressing one or more of pyruvate carboxylases such as PYC2, PYC1 in *S. cerevisiae* and acetyl-coenzyme A synthetase genes such as ACS1 in *S. cerevisiae*; or reducing expression of gene encoding alcohol dehydrogenase, such as ADH2 gene of *S. cerevisiae*.

In another embodiment, ethanol is first produced from sugar source as hexose or pentose and then ethanol is further utilized to glycolic acid. In this latter case the deletion of alcohol dehydrogenase is not desired but instead ethanol utilization should be directed towards the glyoxylate cycle and glycolic acid production.

If the host organism chosen for glycolic acid production is capable of further utilizing glycolic acid it is necessary to also attenuate the genes responsible for these enzyme reactions. E.g. some microbes are known to have glycolate oxidase which oxidases glycolic acid to glyoxylate. In addition glycolic acid production can also be reduced if the host has enzymes other than glyoxylate reductase utilizing glyoxylate. Deletion of malate synthase was already described above as an example how glyoxylate cycle needs to be modified to produce glycolic acid. In addition to malate synthase some fungi are known to have e.g. glyoxylate oxidase, which would need to be deleted in order to produce glycolic acid efficiently.

In one embodiment the cell has been further modified by any combination of the above described modifications.

One embodiment of this invention is also a method for producing glycolic acid. In the method a eukaryotic cell encoding glyoxylate reductase is cultured in conditions allowing the expression the glyoxylate reductase gene, producing and secreting the glycolic acid and optionally recovering the glycolic acid from said medium.

In the production process of the invention, the fungus is cultivated in a growth and production medium that includes a carbon source and typical nutrients required by the particular host, including but not limited to a source of nitrogen (such as amino acids, proteins, inorganic nitrogen sources such as ammonia or ammonium salts), and various vitamins and minerals. Alternatively, more than one different carbon source can be used.

Carbon source contains a sugar which can be hexose or pentose. Hexose can be e.g. glucose, fructose, mannose, or galactose and oligomers of glucose such as maltose, maltotriose, isomaltotriose, starch or cellulose. Examples of pentoses are xylose, xylan or other oligomer of xylose, and preferably also other carbon containing compounds to provide for growth and energy. The medium may also contain ethanol, glycerol, acetate, or amino acids, or any mixture thereof, preferably ethanol or acetate, most suitably ethanol, which further components can also function as carbon sources.

The carbon substrates may be provided as pure substrates or from complex sources. The xylose containing sugars are suitably hydrolysates of plant biomass e.g. hemicellulosecontaining biomass, such as lignocellulose. In addition, the medium may consist of or contain complex, poorly defined elements, such as would be present in relatively inexpensive sources like black liquor, corn steep liquor or solids, or molasses. In case of oligomeric sugars, it may be necessary to add enzymes to the fermentation broth in order to digest these to the corresponding monomeric sugar. It is also possible to use production hosts, such as filamentous fungus hosts that secrete hydrolytic enzymes enhancing the production of fermentative sugars.

Other fermentation conditions, such as temperature, cell density, selection of nutrients, and the like are not considered to be critical to the invention and are generally selected to be suitable for the cell used and to provide an economical process. Temperatures during each of the growth phase and the production phase may range from above the freezing temperature of the medium to about 50° C., although the optimal temperature will depend somewhat on the particular micro-organism. A preferred temperature, particularly during the production phase, is from about 25 to 30° C.

The pH of the process may or may not be controlled to remain at a constant pH, but should be between 1.5 and 6.5, depending on the production organism. In one embodiment the culturing pH is below 6, preferably below 5.5, below 5.0, below 4.5, below 4.0, below 3.5, below 3.0, below 2.5 and even below 2.0, until pH 1.5. Depending on the production organism the lower limit of the pH may vary between 1.5 and 4. Preferred pH of the culture media is 1.5 to 5, more preferably 2 to 4 and most preferably 2 to 3. In one embodiment the culture medium contains no buffering agent.

According to an embodiment of the invention, the pH is controlled to a constant pH of 3.5 to 5.5. Suitable buffering agents for regulating or buffering pH are basic materials that neutralize glycolic acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here. It is within the scope of the invention, however, to allow the pH of the fermentation medium drop from a starting pH that is typically 6 or higher, to below the pKa of the acid fermentation product, such as in the range of about 3 to about 4.

The fermentation is conducted aerobically or microaerobically. If desired, specific oxygen uptake rate can be used as a process control. The process of the invention can be conducted continuously, batch-wise, or some combination thereof.

During the fermentation glycolic acid is excreted out from the cells into the growth medium from which it may be recovered without disrupting the cells.

In one embodiment of the invention a cell described above is cultured and glycolic acid is recovered. Glycolic acid can be recovered from the fermentation medium by e.g. ion exchange chromatography or reactive extraction or it can be polymerized in the fermentation medium and recovered thereafter.

One embodiment of the invention is the use of eukaryotic host cells or eukaryotic organisms in production of glycolic acid or as a starting organism for preparation a production host suitable for production of glycolic acid. In preferred embodiment the eukaryotic organism is a fungal cell, preferably a yeast or filamentous fungus. The eukaryotic organism may be modified as described here and is suitable for the method as described here.

The invention is illustrated by the following non-limiting examples. It should be understood, however, that the embodiments given in the description above and in the examples are for illustrative purposes only, and that various changes and modifications are possible within the scope of the invention.

EXAMPLES

Example 1

A. Construction of a *S. cerevisiae* Strain Able to Produce Glycolic Acid (Selfreplicating Plasmids)

Figure 1:
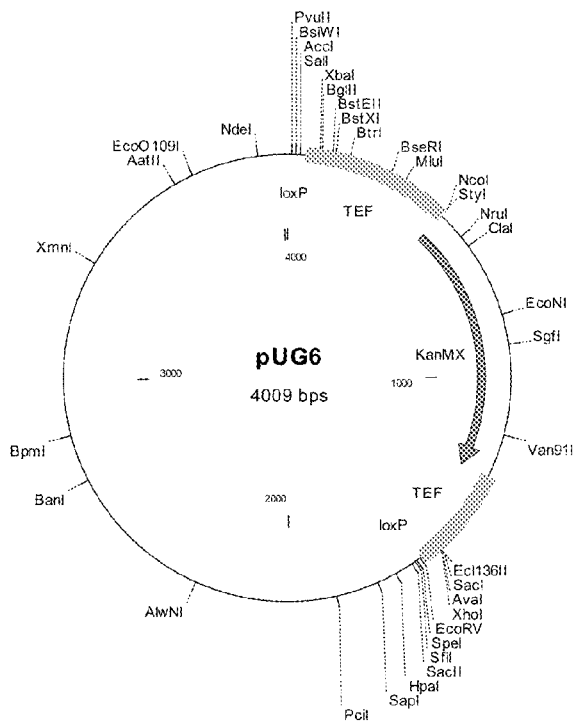
FIG. 1. is a diagrammatic representation of plasmid pUG6 containing G418 gene, KanMX, between loxP sites, which can be used to loop out the KanMX resistance gene from the genomic integration site after Cre recombinase activation.
Figure 2:
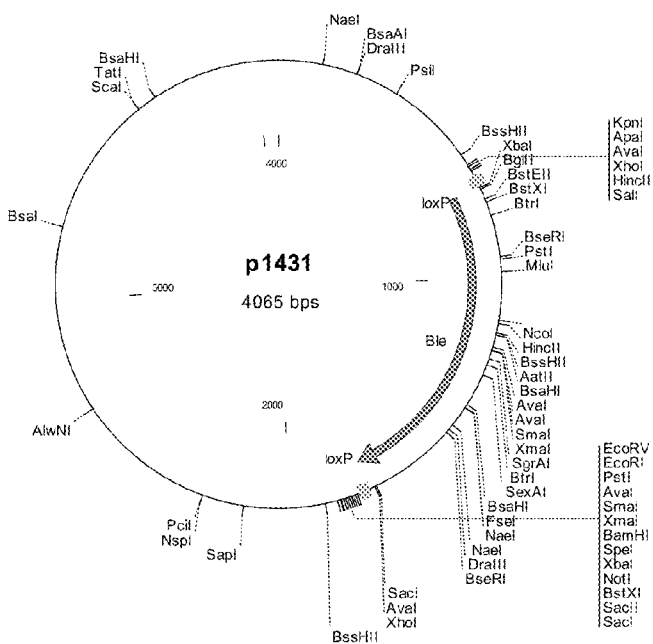
FIG. 2. is a diagrammatic representation of plasmid p1431 which is similar as the plasmid in FIG. 1 except that instead of KanMX marker plasmid has BLE marker for bleomycin (Zeocin) resistance.

The *Saccharomyces cerevisiae* malate synthase gene MLS1 (GenBank accession number NM_001182955) and DAL7 (GenBank accession number NM_001179553) was knocked out from the *S. cerevisiae* strains CEN.PK2 and CEN.PK113-1A. MLS1 deletion cassette was constructed by PCR using primer pair MLS1fwd (SEQ ID NO: 5) and MLS1rev (SEQ ID NO: 6) to amplify loxP-KanMX-loxP fragment of the pUG6 plasmid (FIG. 1) (Guldener et al., 1996). In addition to the 20/23 bp long body annealing to loxP-KanMX-loxP fragment of the pUG6 plasmid, primers contained 40 bp flanks homologous to the sequence outside the *S. cerevisiae* MLS1 for enabling the deletion of MLS1 gene by homologous recombination. The deletion cassette for the other malate synthase gene, DAL7, was constructed in a similar way by PCR with primer pair ScDAL7f (SEQ ID NO: 7) and ScDAL7r (SEQ ID NO: 8) which consisted of 20/23 bp long body annealing to pUG6 plasmid and 40 bp flanks outside the DAL7 for enabling the deletion of the *S. cerevisiae* DAL7 gene. The MLS1 and DAL7 deletion cassettes were transformed to CEN.PK2 (H1346) strain and to CEN.PK113-1A (H3675) strain where the latter is capable to utilize xylose. Deletion fragments included the KanMX gene conferring the ability to grow on media containing G418 (Geneticin). The double deletion strain where MLS1 and DAL7 were both knocked out was constructed in a similar manner except that p1431 (FIG. 2) plasmid instead of pUG6 was used as a template. p1431 is a modification of pUG6 where the KanMX resistance gene has been replaced by BLE marker gene. The MLS1 and DAL7 deletion cassettes were introduced to *S. cerevisiae* strains CEN.PK2 and CEN.PK113-1A in separate transformation procedures. DAL7 deletion fragment included the BLE gene conferring the ability to grow on media containing Zeocin. In order to verify the MLS1 and DAL7 deletions, yeast colony PCR and sequencing reactions were carried out with the primer pairs MLS1seqf (SEQ ID NO: 9), MLS1seqr (SEQ ID NO: 10) and MLS2seqf (SEQ ID NO: 11), MLS1seqr (SEQ ID NO: 12) respectively.

All deletion cassettes contained loxP sites in front and after the marker genes. The loxP sites function as a specific target site for the Cre DNA recombinase enzyme (Güldener et al., 1996). Cre catalyzes DNA recombination leading up to the cleavage of loxP sites. Cre recombinase was expressed in *S. cerevisiae* by transforming the Cre expression plasmid pSH47 (Güldener et al., 1996) into the yeast cell. Plasmid pSH47 conferred the ability to grow in the absence of uracil. In order to activate Cre recombinase the MLS1Δ and DAL74 strains and the double knock-out MLS1Δ, DAL7Δ strain were cultured on a media containing galactose as a carbon source to activate the recombinase. Once the resistance marker had looped out and the ability to grow on media containing G418 and/or Zeocin the strains were cultivated on a rich media (YPD) without selection in order to lose the pSH47 plasmid. Once the strains had lost the ability to grow on media lacking uracil the strains were named as presented in Table 2.

Figure 3:
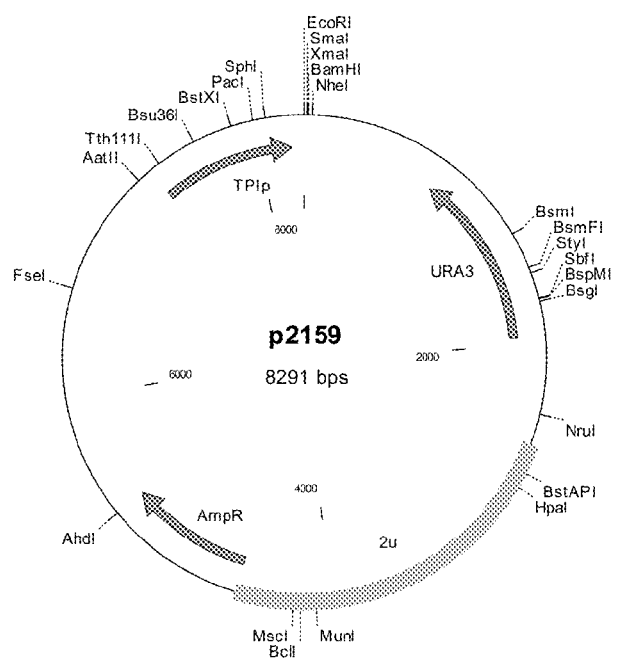
FIG. 3. is a diagrammatic representation of plasmid p2159 which is a constitutive expression plasmid for yeast. It has TPI promoter and URA3 marker gene.
Figure 4:
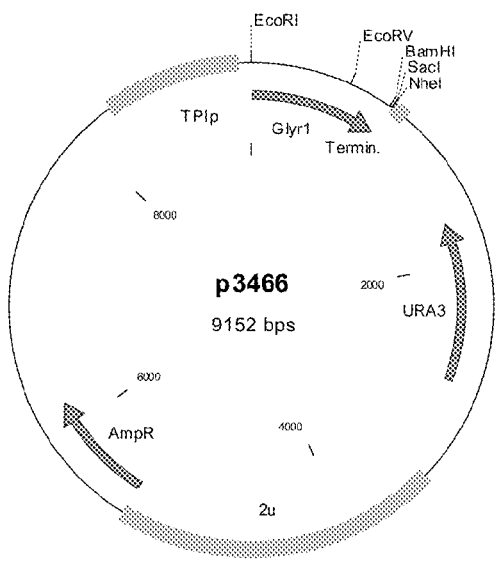
FIG. 4. is a diagrammatic representation of plasmid p3466 where glyoxylate reductase GLYR1 is expressed under TPI promoter.

The original *Arabidopsis thaliana* glyoxylate reductase, GR1 (SEQ ID NO: 1) which codes for the protein GR1 (SEQ ID NO: 3) was codon optimized for *S. cerevisiae* by GenScript (GenScript, USA) and the codon optimized form of the sequence was renamed GLYR1 (SEQ ID NO: 2), which codes for the protein GLYR1 (SEQ ID NO: 3). GLYR1 was ordered and received so that it had additional 5' BamHI and 3' EcoRI sites. GLYR1 was ligated into the EcoRI and BamHI sites between the TPI promoter and polyA terminator of the p2159 vector (FIG. 3), generating plasmid p3644 (FIG. 4). Plasmid p3644 was transformed to *Saccharomyces cerevisiae* CEN.PK2 derived strains H3772, H3773 and H3774 to generate strains H3783, H3784 and H3785 and to CEN.PK113-1A derived strains H3775, H3776 and H3777 to generate strains H3788, H3789 and H3790 (Table 2). Plasmid p3644 conferred the ability to grow in the absence of uracil. Strains were tested for glycolic acid production and as an example, the results of flask cultivations of strain H3790 are presented in the Table 3.

All yeast transformations were carried out with the Gietz method (Gietz and Woods (2002) Transformation of yeast by the LiAc/SS carrier DNA/PEG method. Methods in Enzymology 350: 87-96). The proofreading DNA polymerase Phusion (Thermo Fisher Scientific Inc., Finland) was used for all PCR reactions.

Example 1B

Construction of a *S. cerevisiae* Strain Able to Produce Glycolic Acid (Integrated Cassettes)

Plasmids such as those described in Example 1A are linearized using restriction enzymes, in such a way that the 2 micron sequence (or autonomously replicating sequence, ARS, if appropriate) is deleted from the fragment containing the GLYR1 expression cassette and selectable marker (e.g. KanMX or URA3). These linearized fragments are then used to transform *S. cerevisiae*, with the result that the fragment is integrated into the genome. Integration may be random, or may also occur at a location for which there is homologous sequence present on both the fragment and in the genome. The plasmids may be modified to include specific sequences for targeted integration into the genome at the site of a specific gene, such as HO-locus.

Integration of the GLYR1 gene into the *S. cerevisiae* HO-locus was carried out by first constructing a cassette including GLYR1 under TPI promoter and HO-segments. GLYR1 was first amplified by PCR from p3644 (FIG. 4) with the primer pair ScGLYRp3466-SalIf (SEQ ID NO: 13) and ScGLYRp3466-SalIr (SEQ ID NO: 14) including SalI sites. The product from the PCR reaction was ligated into the TOPO-TA plasmid (Invitrogen, USA) according to the manufacturer's protocol and transformed into *E. coli*. Purified TOPO-TA plasmids were digested with SalI and the TPI-GLYR1-poly-A fragment was ligated into the SalI site of the p3532 (FIG. 5) which has HO-poly-kanMX4-HO fragment (Voth et al., 2001). To verify the correct composition of the plasmid, colony PCR was carried out. The integration cassette was prepared by PCR using modified p3532 plasmid with GLYR1 as a template and HOr-HOlf (SEQ ID NO: 15) and HOr-HOlr (SEQ ID NO: 16) as a primer pair. Resulting deletion fragment can be transformed by homologous integration to any of the strains presented in Examples 1-6 and KanMX gene of the deletion fragment confers the ability to grow on media containing G418. The strain H3777 where the GLYR1 fragment was integrated, generated strain H3913 and the strain H3847 with integrated GLYR1 generated strain H3963. The successful transformation can be seen as an increase in glyoxylate reductase activity compared to the strains where GLYR1 is not introduced.

Example 2

Construction of a *S. cerevisiae* Strain Able to Produce Glycolic Acid with High Yield Strains producing glycolic acid such as those described in examples 1A and 1B can be further modified in order to increase the glycolic acid production. This is possible by increasing flux towards glyoxylate cycle and by overexpressing the genes essential for the pathway.

Figure 5:
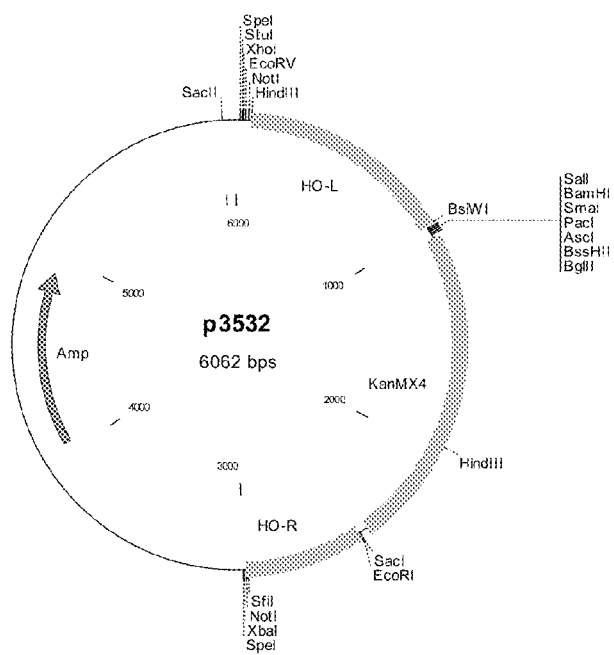
FIG. 5. is a diagrammatic representation of plasmid p3532 where kanMX marker is between the HO-L and HO-R sites which can be used for targeted integration in *S. cerevisiae*.
Figure 6:
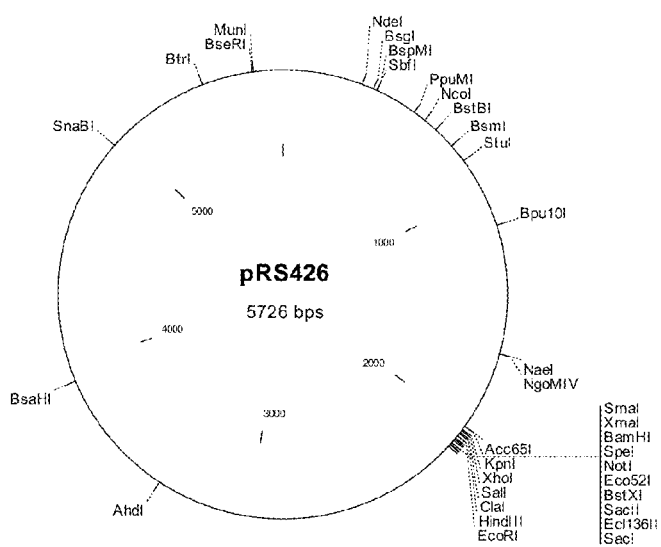
FIG. 6. is a diagrammatic representation of plasmid pRS426 which has URA3 marker gene and can be used as a backbone vector for constructing expression and deletion cassettes by homologous recombination in *S. cerevisiae*.

The overexpression of endogenous isocitrate lyase, ICL1, and deletion of cytosolic NADP-specific isocitrate dehydrogenase, IDP2 (GenBank accession number NM_001182061.1), were carried out by a single integration cassette (FIG. 5). The ICU gene was amplified by PCR using genomic DNA from H3675 strain as a template. The primer pair ICL1fwd (SEQ ID NO: 17) and ICL1rev (SEQ ID NO: 18) including flanks for homologous recombination with p2159 was used in the PCR reaction. Amplified ICL1 fragment together with EcoRI and BamHI digested p2159 plasmid were transformed to *S. cerevisiae* H1346 strain were the vector was constructed by homologous recombination. Transformed yeast cells were screened by growth in the absence of uracil. Recombined plasmids were rescued from yeast and transformed to *E. coli* for plasmid amplification. In order to find the correct plasmid constructs, colony PCR was carried out with the primer pair EcoRI-102fwd (SEQ ID NO: 19) and BamHI+27rev (SEQ ID NO: 20). The TPI-ICL1-poly-A fragment was amplified from correct plasmid construct by PCR with the primer pair Flank19 TPI-ICL1-PolyAf (SEQ ID NO: 21) and Flank-TPI-ICL1-PolyAr (SEQ ID NO: 22). The primer pair included flanks for homologous recombination with the loxP-KanMX-loxP fragment and pRS426 shuttle vector (Christianson et al., 1992) (renamed p2974), which was used as a backbone for cassette construction (FIG. 6).

Figure 7:
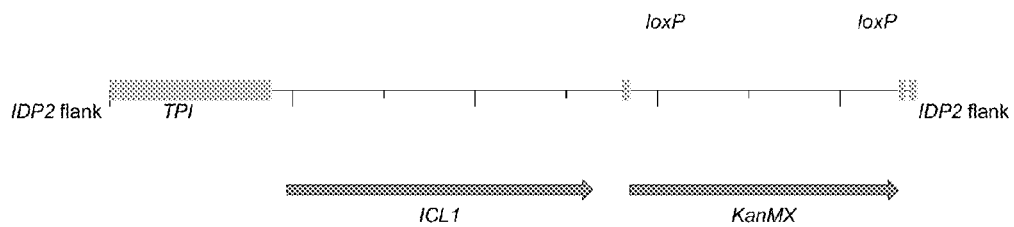
FIG. 7. is a diagrammatic representation of *S. cerevisiae* isocitrate dehydrogenase (IDP2) deletion cassette which in addition to the deletion over expresses *S. cerevisiae* isocitrate lyase (ICL1) gene. The cassette has KanMX marker between the loxP-sites.

The loxP-KanMX-loxP fragment was amplified by PCR using primer pair Flank-KanMXfwd (SEQ ID NO: 23) and Flank-KanMXrev (SEQ ID NO: 24) and the pUG6 plasmid (FIG. 1) as a template. The primer pair included flanks for homologous recombination with the TPI-ICL1-poly-A fragment and pRS426 plasmid. For constructing the cassette expressing ICU and deleting IDP2, EcoRI and XhoI digested pRS426 plasmid and TPI-ICL1-poly-A and loxP-KanMX-loxP fragments were transformed and recombined in H1346 strain. Constructed plasmid was then extracted and transformed into *E. coli*. The correct plasmid composition was confirmed by colony PCR and sequenced with the primer pair Check-IDP2-del-ICL1-f (SEQ ID NO: 25) and Check-IDP2-del-ICL1-r (SEQ ID NO: 26). The cassette expressing ICU and deleting IDP2 (FIG. 7) was amplified from the correct plasmid with the primer pair IDP2-ICL1-f (SEQ ID NO: 27) and IDP2-ICL1-r (SEQ ID NO: 28) including the flanks for homologous recombination into IDP2-locus.

Constructed strain H3947 was used for glycolic acid production after the plasmid p3644 was transformed to the strain. The resulting strain was named H3846 (Table 2). The results of glycolic acid production of the flask cultivations of the strain H3846 are presented in the Table 3.

TABLE 2

Modifications of yeast strains.

Modifications of the H1346 strain.

| Modifications of the H1346 S. cerevisiae strain | Strain number |
|---|---|
| H1346 (mls1Δ) | H3772 |
| H1346 (dal7Δ) | H3773 |
| H1346 (mls1Δ, dal7Δ) | H3774 |
| H1346 (p3644, mls1Δ) | H3783 |
| H1346 (p3644, dal7Δ) | H3784 |
| H1346 (p3644, mls1Δ, dal7Δ) | H3785 |
| H1346 (mls1Δ, dal7Δ, idp2Δ::ICL1) | H3911 |
| H1346 (mls1Δ, dal7Δ, idp2Δ::ICL1, pgi1Δ) | H3965 |
| H1346 (p3644, mls1Δ, dal7Δ, idp2Δ::ICL1, pgi1Δ) | H3973 |

Modifications of the H3675 strain.

| Modifications of the xylose utilizing H3675 S. cerevisiae strain | Strain number |
|---|---|
| H3675 (mls1Δ) | H3775 |
| H3675 (dal7Δ) | H3776 |
| H3675 (mls1Δ, dal7Δ) | H3777 |
| H3675 (p3644, mls1Δ) | H3788 |
| H3675 (p3644, dal7Δ) | H3789 |
| H3675 (p3644, mls1Δ, dal7Δ) | H3790 |
| H3675 (p3644, mls1Δ, dal7Δ, idp2Δ::ICL1) | H3846 |
| H3675 (mls1Δ, dal7Δ, idp2Δ::ICL1) | H3847 |
| H3675 (HO-locus::GLYR1, mls1Δ, dal7Δ) | H3913 |
| H3675 (HO-locus::GLYR1, mls1Δ, dal7Δ, idp2Δ::ICL1) | H3963 |
| H3675 (p3644, mls1Δ, dal7Δ, idp2Δ::ICL1, reg1Δ) | H3994 |

Modifications of the K. lactis strain.

| Modifications of the K. lactis | Strain number |
|---|---|
| K. lactis (mls1Δ, idp2Δ) | H3976 |
| K. lactis (p4185, mls1Δ, idp2Δ) | H3986 |
| K. lactis (mls1Δ::ALD6, idp2Δ) | H4156 |
| K. lactis (mls1Δ::ALD6::ACS1, idp2Δ) | H4157 |
| K. lactis (p4185, mls1Δ::ALD6::ACAS1, idp2Δ) | H4158 |

TABLE 3

Glycolic acid production of selected yeast strains.

| Organism | Strain number | Used carbon sources | Day 1 | Day 2 | Day 3 | Day 6 |
|---|---|---|---|---|---|---|
| S. cerevisiae | H1346 | 2% glucose | 0 | 0 | 0 | 0 |
| | | 2% ethanol + 2% glycerol | 0 | 0 | 0 | 0 |
| S. cerevisiae | H3675 | 2% xylose | 0 | 0 | 0 | 0 |
| | | 2% ethanol + 2% glycerol | 0 | 0 | 0 | 0 |
| S. cerevisiae | H3790 | 2% glucose | 0 | 0 | 0 | 0 |
| | | 2% xylose | 0 | 0 | 0 | 0 |
| | | 2% ethanol + 2% glyserol | 0 | 1.6 | 0.34 | 0.45 |
| S. cerevisiae | H3846 | 2% glucose | 0.09 | 0.28 | 0.28 | 0.28 |
| | | 2% ethanol | 0.71 | 0.78 | 0.78 | — |
| S. cerevisiae | H3973 | 1.9% fructose + 0.1% glucose | 0 | 0 | 0.46 | 0.54 |
| K. lactis | H3986 | 2% xylose + 2% ethanol | 0.45 | 0.83 | 1.77 | 1.88 |
| | | 2% xylose + 2% ethanol + 5 g l$^{-1}$ ethanol added daily | 0.46 | 0.93 | 1.58 | 2.94 |

As can be seen from the above results, flask cultivations already provide advantageous results. However, even higher yields could be obtained when cultivating in a fermentor instead of flasks (Example 14).

Figure 8:
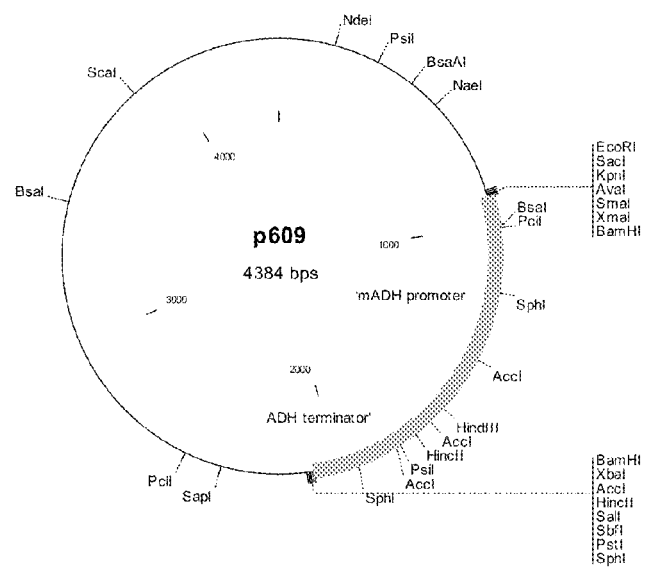
FIG. 8. is a diagrammatic representation of plasmid p609 which is a constitutive expression plasmid for yeast. It has mADH promoter and URA3 marker gene.

Example 3. Further Construction of a S. cerevisiae Strain Able to Produce Glycolic Acid with High Yield It is possible to further modify the host in order to increase glycolic acid production. This can be done by directing the flux towards glyoxylate cycle and by overexpressing the genes essential for the pathway. These overexpressed genes can be such as aconitase (ACO1) which converts citrate into isocitrate via cis-aconitate that is further converted into glyoxylate in the glyoxylate cycle. The ACO1 gene was amplified by PCR using genomic DNA from S288c (H190) strain as a template. The primer pair ACO1HindIIIf (SEQ ID NO: 29) and ACO1HindIIIr (SEQ ID NO: 30) introducing HindIII sites was used and the fragment was ligated into the HindIII site between the mADH promoter and terminator of the p609 plasmid (FIG. 8). The correct plasmid composition was confirmed by colony PCR and sequenced and it can be used for transformation as such or the fragment including the promoter and terminator sequence can be further used for deletion cassette or integration constructs which contain flanks for homologous recombination. This resulting fragment can be used for genomic integration of the gene which can be done similarly as presented in Example 1B and 2 or overexpressed genes can also be introduced as plasmids as described in the Example 1A. The constructs were checked by PCR and the overexpression of the said gene was confirmed by enzyme assays. After the GLYR1 was transformed to the strains as described in Examples 1A and 1B the strain was tested for glycolic acid production as described in the Example 9.

Example 4. Construction of a S. cerevisiae Glycolic Acid Producing Strain with Reduced Ethanol Production Increase in flux towards glycolic acid can also be achieved by knocking out genes directing the flux in unwanted directions. ADH2 gene of the S. cerevisiae (GenBank accession number NM_001182812) was knocked out in order to decrease ethanol formation. The deletion construct was amplified by PCR using primers ADH2delflankKpnINotIf (SEQ ID NO: 31), ADH2delflankEcoRISalIr (SEQ ID NO: 32) for the first flanking fragment and ADH2delflank2EcoRIBamHIf (SEQ ID NO: 33), ADH2delflank2SpeIr (SEQ ID NO: 34) were used for the second flanking fragment. The first ADH2 fragment was then digested with KpnI and SalI restriction enzymes and ligated with the pRS426 vector (FIG. 6) which has been linearized with the same restriction enzymes KpnI and SalI. The resulting plasmid was redigested with EcoRI and SpeI and the second ADH2 flanking fragment, first digested with these same enzymes EcoRI and SpeI, was ligated to the vector. The resulting plasmid with pRS426 backbone and both ADH2 flanks was then digested with SalI and EcoRI. The loxP-KanMX-loxP fragment was amplified by PCR by primer pair loxPkanMX-loxP_SalIf (SEQ ID NO: 35) and loxP-kanMX-loxP_EcoRIr (SEQ ID NO: 36) using plasmid pUG6 (FIG. 1) as a template. The resulting fragment was digested with SalI and EcoRI and ligated between the SalI and EcoRI sites of the ADH2 flanking regions. The construct was checked by primers pRS426XhoIcutFseq (SEQ ID NO: 37), pRS426SpeIcutRseq (SEQ ID NO: 38) and loxPKanMX-loxPseqF (SEQ ID NO: 39).

Correct deletion cassette was then cleaved with NotI and the resulting fragment was transformed to S. cerevisiae by homologous recombination. Overexpression of selected genes is also possible with the same deletion fragment as a fragment expressing the gene with promoter and terminator can be introduced between the ADH2 flank and loxP-KanMX-loxP fragment either by homologous recombination or by ligation after digestion with suitable restriction enzymes. The overexpressed gene(s) can be e.g. pyruvate carboxylase (PYC1 or PYC2) or any of the genes which overexpression is described in the Examples 2, 3, 5 or 6. The constructs can be then checked by PCR or sequencing and deletion of the said gene can be confirmed by enzyme assay where the activity of alcohol dehydrogenase is decreased and the activity of the overexpressed gene is increased.

After the GLYR1 was transformed to the strains as described in Examples 1A and 1B the strains were tested for glycolic acid production as described in Example 9.

Example 5. Construction of a S. cerevisiae Glycolic Acid Producing Strain with Increased NADPH Availability S. cerevisiae PGI1 (GenBank accession number NM_001178544) knock-out strain was constructed in order to balance the NADPH availability as NADPH is required by the glyoxylate reductase reducing glyoxylate into glycolic acid. PGI1 flanks were amplified from genomic DNA of S. cerevisiae S288c (H190) strain. Primers PGIflankKpnINotIf (SEQ ID NO: 40) and PGIflankEcoRISalIr (SEQ ID NO: 41) were used for the construction of the first PGI1 flank fragment. The second PGI1 flank fragment was amplified with primers PGIflank2EcoRIBamHIf (SEQ ID NO: 42) and PGIflank2SpeIr (SEQ ID NO: 43). In addition, the loxP-KanMX-loxP fragment was amplified from the pUG6 vector (FIG. 1) with primer pair loxP-kanMX-loxP_SalIf (SEQ ID NO: 35) and loxP-kanMX-loxP_EcoRIr (SEQ ID NO: 36). The KpnI and EcoRI digested PGI1 flank1 and the pRS426 vector (FIG. 6) linearized with the same restriction enzymes, KpnI and EcoRI, were first ligated together. As a next step, the resulting plasmid as well as the PGI1 flank 2 fragment were digested with EcoRI and SpeI and ligated together. The resulting plasmid with the pRS426 backbone and both PGI1 flanks and the loxP-KanMX-loxP fragment were digested with SalI and EcoRI and ligated together. The final construct was checked by colony-PCR with primers loxP-kanMX-loxP_EcoRIr (SEQ ID NO: 36) and pRS426XhoIcutFseq (SEQ ID NO: 37) and sequenced with primers pRS426XhoIcutFseq (SEQ ID NO: 37) and pRS426SpeIcutRseq (SEQ ID NO: 38) and the correct vector construct was named as p4115.

The PGI1 deletion cassette was released by NotI digestion from p4115 plasmid and transformed into strain H3911 resulting strain H3965 (Table 2). The PGI1 negative mutants were screened based on glucose toxicity. The loxP-KanMX-loxP marker of the PGI1 deletion cassette was looped out from the PGI1 deficient strain H3965 by using the Cre recombinase plasmid (p902). After the GLYR1 was transformed to the strain as described in Example 1A the strain was named as H3973 and it was used for glycolic acid production (Table 3).

PGI1 can be replaced by some other genes such as cytosolic aldehyde dehydrogenase (ALD6) and/or acetyl-coA synthase (ACS1) (Example 16) and/or any of the genes which overexpression is described in the Examples 2, 3, 4 or 6. Different combinations of overexpressed genes can be used under different promoters and terminators.

Example 6. Construction of S. cerevisiae Strain where Glyoxylate Cycle Regulation has been Affected in Order to Get Higher Glycolic Acid Yields REG1 of S. cerevisiae is a regulatory subunit of type 1 protein phosphatase Glc7p, involved in negative regulation of glucose-repressible genes. The gene was deleted in order to decrease the glucose repression of the glyoxylate cycle. The REG1 (GenBank accession number NM_001180336) deletion was done by using the primer pair Reg1delfwd (SEQ ID NO: 44) and Reg1delrev (SEQ ID NO: 45) for PCR where pUG6 (FIG. 1) plasmid was used as a template. The resulting loxP-KanMX-loxP fragment with flanks homologous to the sequence upstream and downstream of the REG1 gene was transformed to yeast and the transformants were selected based on the G418 resistance. The strain H3847 was named as H3994 after the REG1 deletion (Table 2). After the GLYR1 was transformed to the strains as described in Examples 1A and 1B the strains were used for glycolic acid production as described in Example 9.

Example 7. Construction of a K. lactis Glycolic Acid Producing Strain

Vector for expression of glyoxylate reductase in K. lactis: The pJJH958r (FEMS Yeast Res (2010) 333-342) was digested with KpnI to remove the CreR gene with GAL1 promoter and CYC1 terminator and religated. The circular vector, p4150, was then digested with SalI. The GLYR1 gene with TPI1 promoter and terminator from Example 1A was then amplified by PCR to introduce SalI restriction sites and ligated to the SalI site of p4150. The resulting vector, p4185, is a multicopy expression vector for the GLYR1 with URA3 selection.

Deletion of a malate synthase gene in K. lactis: The K. lactis gene with the GenBank accession number CR382126.1 was identified as the gene with highest homology to the S. cerevisiae MLS1 and was deleted following a protocol described previously (FEMS Yeast Res 10 (2010) 333-342). The HIS3 gene of the pJJH955H (FEMS Yeast Res 10 (2010) 333-342) was amplified by PCR using primers K1MLS1 (SEQ ID NO: 46) and K1MLS2 (SEQ ID NO: 47) that had 50 bp flanking regions upstream and downstream the open reading frame of the MLS1 homologue. The PCR product was then transformed to the K. lactis strain Os276 (FEMS Yeast Res 10 (2010) 333-342) and transformants selected for the ability to grow in the absence of histidine. The deletion cassette was then looped out as described previously (FEMS Yeast Res 10 (2010) 333-342). The resulting strain, H3968, was not growing on ethanol medium in contrast to the parent strain.

Deletion of the IDP2 homologue in K. lactis and expression of glyoxylate reductase: The K. lactis gene with the Gene ID: 2894935 was identified as the closest homologue to the S. cerevisiae IDP2 and was deleted in the H3968 in a similar way as the MLS1 homologue described above using the primers K1IDP2F (SEQ ID NO: 48) and K1IDP2R (SEQ ID NO: 49). The resulting strain is H3976. This strain was transformed with the glyoxylate reductase expression vector, p4185, resulting in the strain H3986. The strain was tested for glycolic acid production and the results are shown in Table 3.

Modification of the *K. lactis* CAT8 gene by changing the serine at 661 to glutamine, S661E: The mutation S661E in the *K. lactis* CAT8 gene changes the transactivation activity in a way that the CAT8 is constitutively active (Mol. Cell Biol. 24(2004) 4083-4091). To make this point mutation a CAT8 fragment with the S661E mutation was made by PCR with the primers K1Cat8S661EHind (SEQ ID NO: 50) and K1Cat8revPst (SEQ ID NO: 51). This fragment was then digested with HindIII and PstI and ligated to the HindIII and PstI digested plasmid pJJH955L (FEMS Yeast Res 10 (2010) 333-342). This vector has the LEU2 marker between loxP sites. The CAT8 fragment with the mutation followed by the LEU2 marker was the amplified by PCR with the primers K1Cat8S661Ef (SEQ ID NO: 52) and K1Cat8S661Er (SEQ ID NO: 53) and the PCR product transformed to the H3976. The LEU2 was then looped out as described before and the expression vector for the GLYR1, p4185, transformed. The resulting strain is H3987 and it was used for glycolic acid production as described in Example 9.

Figure 9:
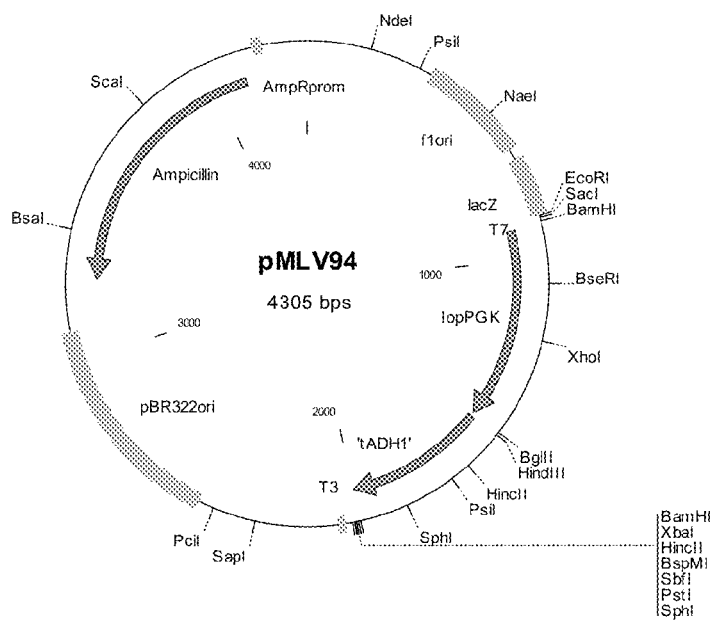
FIG. 9. is a diagrammatic representation of pMLV94 plasmid which has *C. krusei* PGK promoter and *S. cerevisiae* ADH1 terminator.

Example 8. Construction of a *Candida krusei* Strain Able to Produce Glycolic Acid with High Yield Glyoxylate reductase GLYR1 was introduced into *C. krusei* strain ATCC32196 under PGK1 promoter of *C. krusei*. The IoPGK1 promoter was amplified from the genomic DNA of *C. krusei* strain ATCC32196 essentially as described in US 2009/0226989 A1, Sep. 10, 2009. pMLV94 (FIG. 9) is a bacterial plasmid with *C. krusei* PGK promoter and *S. cerevisiae* ADH1 terminator. GLYR1 was amplified by PCR by primer pair BglIIGLYRfwd (SEQ ID NO: 54) and BglIIGLYRrev (SEQ ID NO: 55) introducing BglII sites to the fragment.

Figure 10:
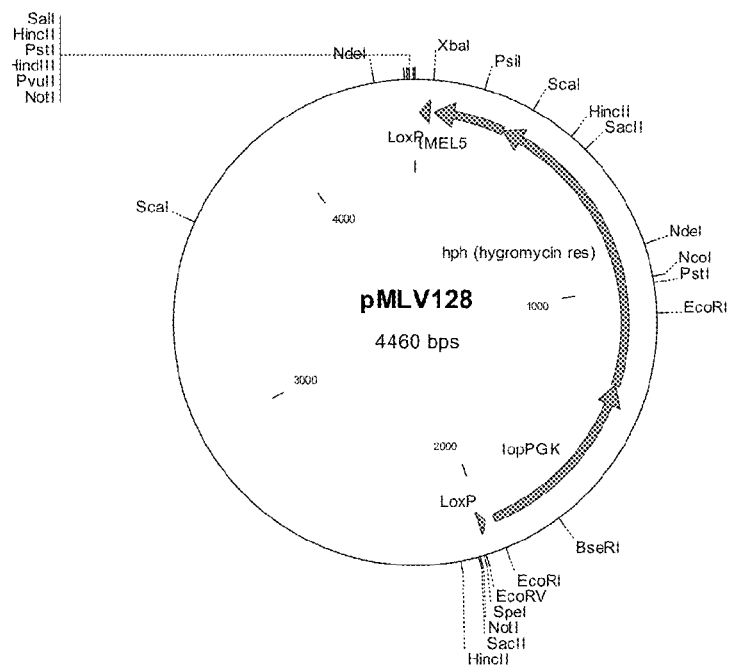
FIG. 10. is a diagrammatic representation of pMLV128 plasmid for *C. krusei* which has hygromycin resistance, hph, marker gene.

After BglII digestion the GLYR1 fragment was ligated to the BglII site of the pMLV94 vector and the resulting plasmid was digested with BamHI to release the 2.0 kb fragment including the promoter and terminator regions and the GLYR1 gene.

pMLV128 plasmid (FIG. 10) containing the loxP-hph-loxP fragment, where hph stands for a gene giving resistance for hygromycin, was digested with PvuII, and BamHI digested prom-GLYR1-term fragment was ligated to the site after its 5' overhangs had been filled-in with Klenow polymerase reaction. The resulting plasmid was digested with NotI in order to release the fragment.

*C. krusei* malate synthase gene (SEQ ID NO: 72), MLS, was identified based on the homology to the *S. cerevisiae* MLS1 gene. The flanks homologous to the genome sequence upstream and downstream of the *C. krusei* MLS1 gene were amplified using primer pair IoMLSflank5fpRS (SEQ ID NO: 56), IoMLSflank5rIopPGK (SEQ ID NO: 57) and primer pair IoMLSflank3floxP (SEQ ID NO: 58), IoMLSflank3rpRS (SEQ ID NO: 59). In addition also primer pairs IoMLSflank5fpRS 2 (SEQ ID NO: 73), IoMLSflank5rIopPGK 2 (SEQ ID NO: 74) and primer pair IoMLSflank3floxP_2 (SEQ ID NO: 75), IoMLSflank3rpRS (SEQ ID NO:76) can be used.

All fragments, including the NotI released fragment with promoter-GLYR1-terminator-loxP-hph-loxP, the NotI digested pMLV128 vector and the two MLS1 flanking fragments were combined by homologous recombination in *S. cerevisiae* to produce a cassette with GLYR1 overexpression fragment combined to the hph resistance marker and at least 400-500 bp flanks which were similar to the sequence upstream and downstream of the malate synthase gene of the *C. krusei*. The resulting malate synthase deletion fragment overexpressing GLYR1 was confirmed by sequencing and the 5.0 kb deletion fragment, released by XmaI digestion, was transformed to *C. krusei*. Transformants were plated on YPD plates containing 400 μg ml$^{-1}$ hygromycin for the selection. Correct transformants were analysed by PCR and by enzyme assays where glyoxylate reductase activity was found to be increased. The strain was named as H4154.

Figure 19:
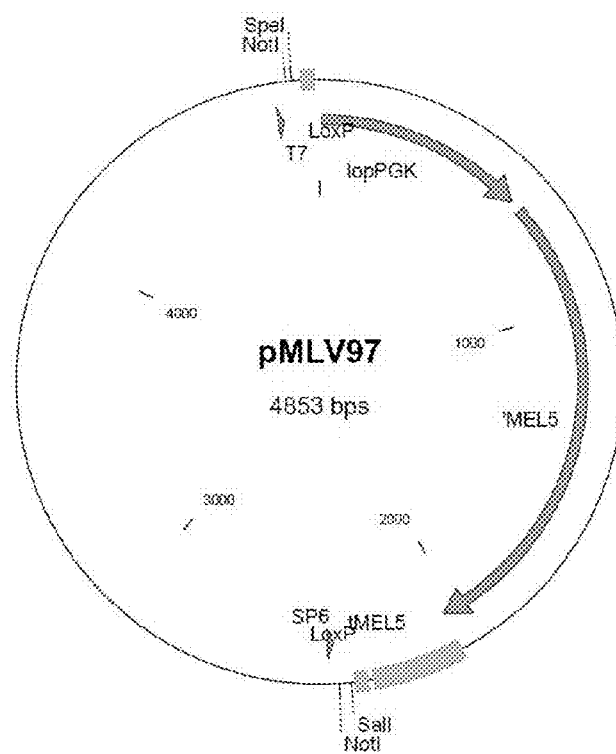
FIG. 19. is a diagrammatic representation of pMLV97 plasmid for *C. krusei* which has MEL marker gene.
Figure 20:
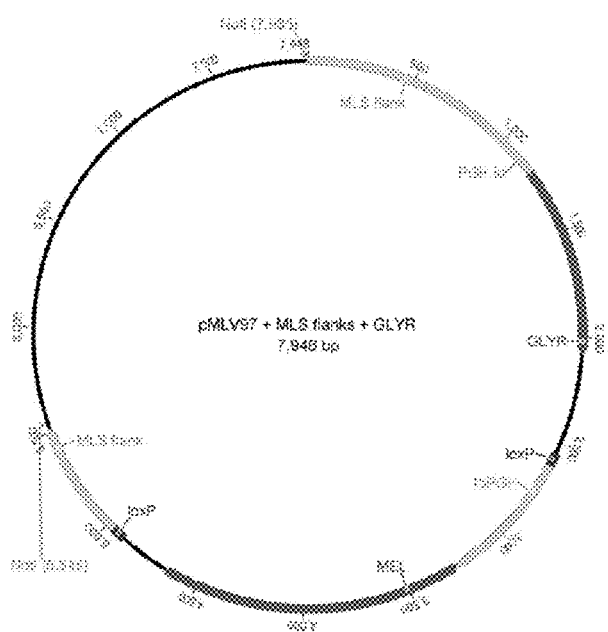
FIG. 20. is a diagrammatic representation of pMLV97 plasmid for *C. krusei* which has MEL marker gene and where MLS flanks and GLYR1 expression cassette have been ligated.

*C. krusei* is diploid and its second copy of malate synthase gene was deleted by using following primer pairs for MLS deletion cassette construction: 221MLS3'fSalI (SEQ ID NO: 77), 222MLS3'rSalI (SEQ ID NO: 78), and 223MLS5'fSpeI (SEQ ID NO: 79), 224MLS5'rSpeIBamHI (SEQ ID NO: 80). The first fragment was digested by SalI and the second fragment by SpeI.

pMVL97 plasmid (FIG. 18) containing the loxP-MEL-loxP fragment, where MEL stands for a gene encoding for α-galactosidase gene which gives the cells carrying the gene a blue colour when plated on a plate containing x-α-gal, was digested with SalI. The SalI digested fragment flanking to the upstream of the *C. krusei* malate synthase gene was ligated to the vector and correct plasmid construct was then further digested with SpeI. The SpeI digested fragment flanking downstream of the MLS gene was ligated to the vector and correct plasmid construct was selected based on the colony-PCR verification. The plasmid construct with MLS flanks was digested with BamHI and the above described GLYR fragment was ligated to the vector. The resulted plasmid (FIG. 19) construct was then sequenced. MLS deletion cassette was cleaved with NotI digestion and the 5.5 kb fragment was purified from the agarose gel.

The 5.5 kb deletion fragment was transformed to *C. krusei* strain where already one copy of the malate synthase gene had been deleted. Transformants were plated on YPD plates containing 300 μg ml$^{-1}$ hygromycin and 40 μg ml$^{-1}$ x-α-gal. The correct transformants were selected among the blue colonies.

Correct transformants were analysed by PCR and by enzyme assays where malate synthase activity was decreased and glyoxylate reductase activity increased. The resulting strain H4155 was not growing on ethanol medium in contrast to the parent strain and the strain *C. krusei* H4154 where only one malate synthase had been deleted. H4154 and H4155 strains expressing glyoxylate reductase were used for glycolic acid production as described in Example 9. The production of glycolic acid is presented in Table 4. The pH of *C. krusei* strain H4155 after two days cultivation was measured to be 2.8 showing that the production of glycolic acid is possible in non-buffered conditions still at low pH.

TABLE 4

Glycolic acid production of *C. krusei*.

| Organism | Strain number | Used carbon sources | Glycolic acid production (g l$^{-1}$) | | |
|---|---|---|---|---|---|
| | | | Day 0 | Day 1 | Day 2 |
| *C. krusei* | ATCC32196 | 2% glucose | 0 | 0 | 0 |
| *C. krusei* (mls1Δ::GLYR1) | H4154 | 2% glucose | 0 | 0 | 0 |
| *C. krusei* (mls1Δ::GLYR1/ mls1Δ::GLYR1) | H4155 | 2% glucose | 0 | 0.424 | 1.629 |

Example 9. Production of Glycolic Acid by Modified Yeast Strains

*K. lactis* H3986 was grown in non-buffered conditions in modified synthetic complete (SC) medium lacking uracil (Sherman F, Fink G, Hicks J B. (1983) Methods in Yeast Genetics. A Laboratory Manual. Cold Springs Harbor Laboratory, Cold Springs Harbor, N.Y.). Xylose (20 g l$^{-1}$) and ethanol (20 g l$^{-1}$) were provided as a carbon source. Yeast was grown in 50 ml SC-URA medium shake flask at 30° C., 200 rpm.

The other yeast strains described in Examples 1-8 were grown in similar conditions with different carbon sources. The integrant strains S. cerevisiae (Example 1B) and C. krusei (Example 8) were grown on SC medium instead of SC medium lacing uracil. Instead of xylose (20 g l$^{-1}$) and ethanol (20 g l$^{-1}$) mix also other carbon sources were tested: glucose, xylose, ethanol, ethanol+glycerol and fructose+glucose in different concentrations. The results of glycolic acid production of some selected strains are presented in Table 3 and the production in modified C. krusei strain is presented in Table 4. The base strains H1346 and H3675 without any additional modifications did not produce glycolic acid (Table 3) according to the HPLC results.

Figure 14:
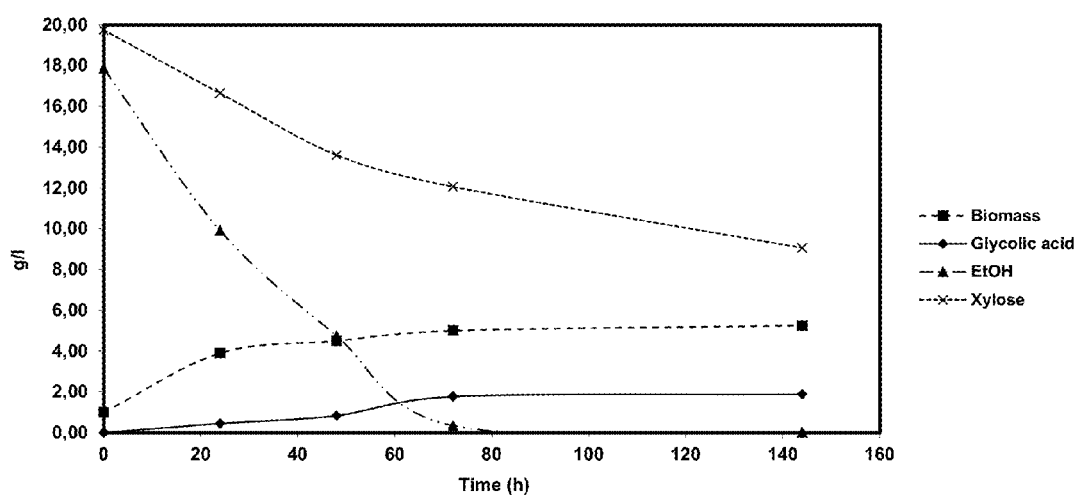
FIG. 14. shows the production of glycolic acid in modified *K. lactis* strain where malate synthase and isocitrate dehydrogenase are deleted and GLYR1 expressed in a plasmid (H3986). The fermentation is done in synthetic medium containing 2% xylose and 2% ethanol. Also biomass and xylose and ethanol amounts are presented in the figure.
Figure 15:
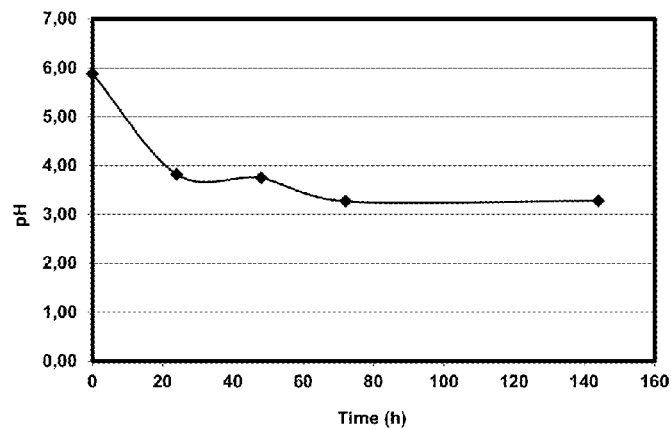
FIG. 15. shows the pH curve of the *K. lactis* strain H3986 fermentation presented in FIG. 14 which was done in unbuffered media.

Extracellular metabolites in cell-free spent culture medium (glycolic acid, ethanol), and xylose were analysed by HPLC on a Fast Acid Analysis Column (100 mm×7.8 mm, BioRad, Hercules, Calif.) linked to an Aminex HPX-87H column (BioRad Labs) with 2.5 mM $H_2SO_4$ as eluent and a flow rate of 0.5 ml min$^{-1}$. The column was maintained at 55° C. Peaks were detected using a Waters 410 differential refractometer and a Waters 2487 dual wavelength UV (210 nm) detector. As an more detailed example the formation of glycolic acid and biomass and the consumption of xylose and ethanol of the K. lactis strain H3986 are presented in FIG. 14 and the pH curve is presented in the FIG. 15.

Figure 16:
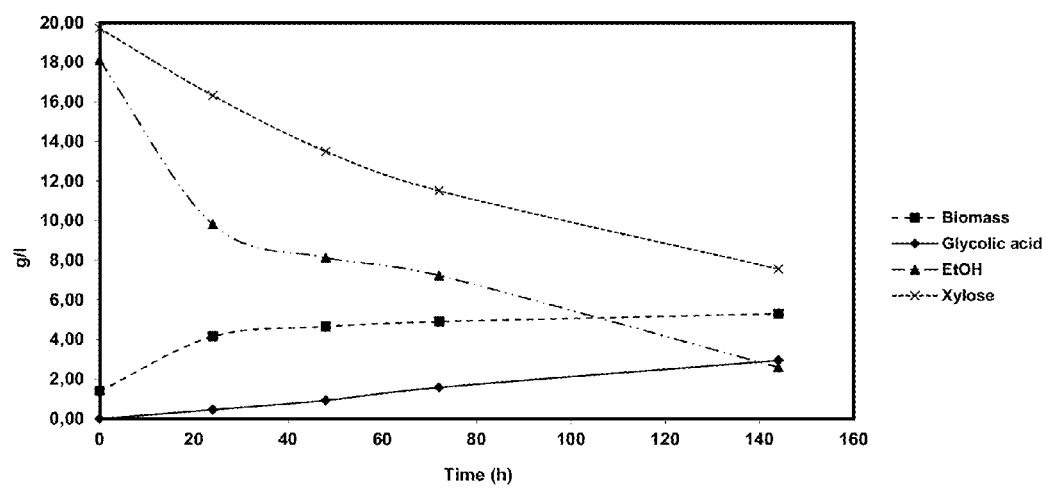
FIG. 16. shows the production of glycolic acid in modified *K. lactis* strain where malate synthase and isocitrate dehydrogenase are deleted and GLYR1 expressed in a plasmid (H3986). The fermentation is done in synthetic medium containing 2% xylose and 2% ethanol and 5 g l$^{-1}$ ethanol was added daily to the culture. Also biomass and xylose and ethanol amounts are presented in the figure.
Figure 17:
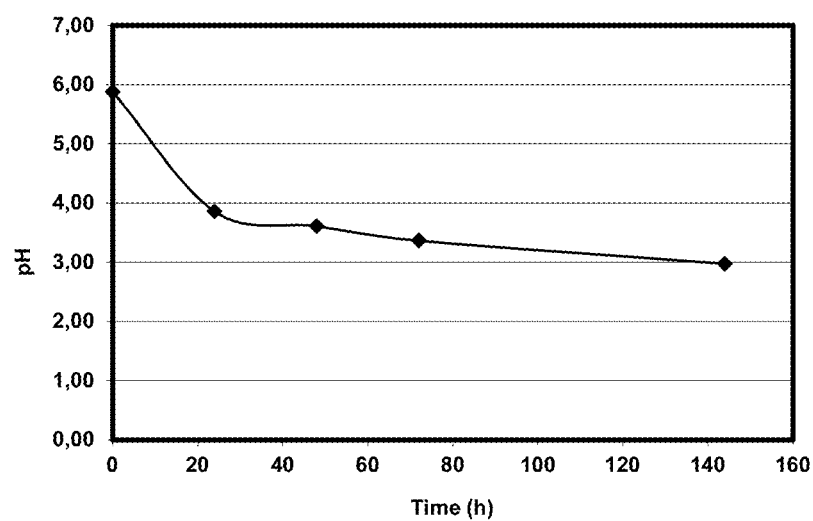
FIG. 17. shows the pH curve of the *K. lactis* strain H3986 fermentation presented in FIG. 16 which was done in unbuffered media.

Example 10. Production of Glycolic Acid by Modified Yeast Strains with Additional Ethanol Since glycolic acid production occurred at the highest rates when ethanol was present as the carbon source, the production of glycolic acid with addition of extra ethanol was demonstrated. Similar experiment as described more closely in the Example 9 was done with the same K. lactis strain H3986 so that in addition to the xylose (20 g l$^{-1}$) and ethanol (20 g l$^{-1}$), 5 g l$^{-1}$ of ethanol was added to each flask daily. The analysis of glycolic acid, ethanol and xylose concentrations in the media was done by HPLC as presented in the Example 8. The formation of glycolic acid and biomass and the consumption of xylose and ethanol are presented in FIG. 16 and the pH curve is presented in the FIG. 17.

Example 11. Construction of A. niger Glycolic Acid Producing Strain

Figure 11:
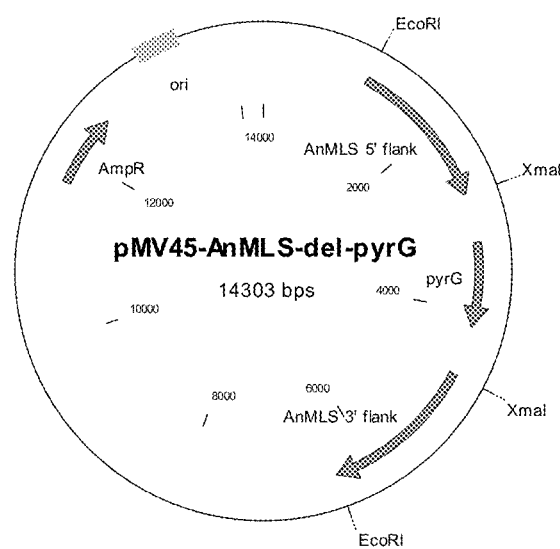
FIG. 11. is a diagrammatic representation of pMV45-AnMLS-del-pyrG plasmid for *A. niger*. The plasmid has flanks for malate synthase deletion and pyrG marker.
Figure 12:
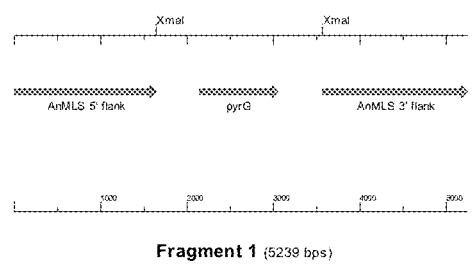
FIG. 12. is a diagrammatic representation of pyrG-MLS deletion cassette for *A. niger*. It has flanks for malate synthase deletion and pyrG marker.

A plasmid pMV45-AnMLS-del-cas (FIG. 10) contained 1633 bp (region −969 . . . +664 from the both sides of the ATG start codon) from the A. niger acuE (malate synthase gene) promoter and ORF, followed by the pyrG gene (including the native pyrG promoter and terminator regions, −500 . . . −1 from ATG and +1 . . . +497 from the stop codon, respectively) and 1671 bp (region −720 . . . +951 from the from the both sides of the TAA stop codon) from A. niger acuE ORF and terminator. The acuE 5' and 3' fragments were obtained by PCR of genomic DNA from A. niger ATCC1015 using primers AnMLS-5'-For (SEQ ID NO: 60) and AnMLS-5'-Rev (SEQ ID NO: 61) and AnMLS-3'-For (SEQ ID NO: 62) and AnMLS-3'-Rev (SEQ ID NO: 63). The pyrG gene fragment was obtained by PCR of genomic DNA from A. niger ATCC1015 using primers pyrG-del-F_n (SEQ ID NO: 64) and pyrG-del-R_n (SEQ ID NO: 65). The proofreading DNA polymerase Phusion (Thermo Fisher Scientific Inc., Finland) was used for all PCR reactions. Construction of the plasmid was performed in three steps. First, plasmid pMV45 was digested by the restriction endonuclease EcoRI (NEB) and amplified A. niger AcuE fragments were digested by the restriction endonuclease EcoRI and XmaI (both NEB). Ligation of digested pMV45 plasmid and A. niger acuE fragments was performed using T4 DNA ligase and the intermediary construct pMV45-AnMLS was obtained. Second, pMV45-AnMLS and amplified pyrG fragment were digested with the restriction endonucleases XmaI (NEB). Ligation was performed using T4 DNA ligase and the intermediary construct pMV45-AnMLS-del-pyrG was obtained. Third, pMV45-AnMLS-del-pyrG was digested with the restriction endonuclease EcoRI (NEB) and the final construct pMV45-AnMLS-del-pyrGcas was obtained (FIG. 11).

A uracil auxotroph A. niger strain An1015-pyrGΔ was generated as described by Mojzita et al. 2010 (Mojzita D, Wiebe M, Hilditch S, Boer H, Penttila M, Richard P: Metabolic engineering of fungal strains for the conversion of D-galacturonate to meso-galactarate. Appl Environ Microbiol 2010, 76:169-175.). An1015-pyrGΔ was transformed with the deletion cassette pMV45-AnMLS-del-pyrG-cas, to generate strain An1015-acuEΔ::pyrG. Transformation was performed using the basic PEG-mediated protoplast transformation method and transformants were screened for integration of the deletion cassette at the acuE locus by growth in the absence of uracil. Deletion of the acuE gene was confirmed by PCR with primers AnMLS-screen-For (SEQ ID NO: 66) and AnMLS-screen-Rev (SEQ ID NO: 67). Strain An1015-acuEΔ::pyrG was identified as a transformant in which the acuE gene had been deleted. The strain had no malate synthase activity which was confirmed by the malate synthase assay (the utilization of acetyl-CoA in the presence of glyoxylate) and it produced less biomass from ethanol than the parent strain on an agarose plate.

Figure 13:
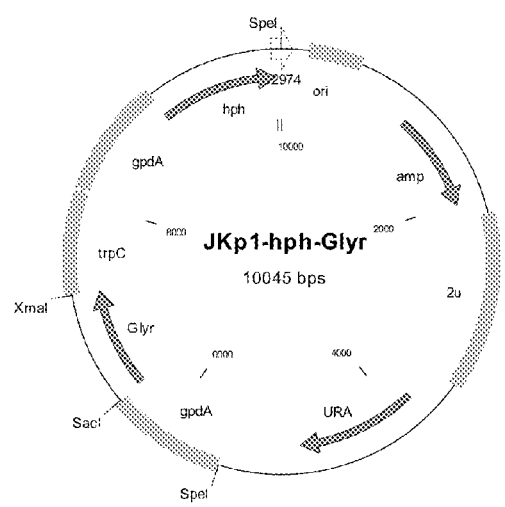
FIG. 13. is a diagrammatic representation of JKp1-hph-Glyr plasmid for *A. niger*. The plasmid is an overexpression vector for GLYR1 gene and it has hygromygin resistance, hph, marker gene in addition to URA3 gene.

Plasmid JKp1-hph-Glyr (FIG. 13) contained hygromycin B phosphotransferase gene (hph) and A. niger codon optimized (by GenScript) GLYR1 gene from A. thaliana (SEQ ID NO: 4) under the gpdA promoter and trpC terminator. The codon optimized GLYR1 (from GenScript) was received with the 5' SacI and 3' XmaI sites. The received GLYR1 gene and the plasmid JKp1-hph were digested with the restriction endonucleases SacI and XmaI (both NEB). Ligation of digested JKp1-hph plasmid and the GLYR1 fragment was performed using T4 DNA ligase and the intermediary construct JKp1-hph-Glyr was obtained. JKp1-hph-Glyr was digested with the restriction endonuclease SpeI (NEB) and digested cassette containing gpdA-GLYR1-trpC-hph was transformed into the An1015-acuEΔ::pyrG strain using the standard fungal transformation methods and transformants were screened for integration of the gpdA-GLYR1-trpC-hph cassette by growth in the presence of hygromycin. Integration of the transformed fragment into the genome was confirmed by PCR with the primers AnGlyrScreenFor (SEQ ID NO: 68) and AnGlyrScreenRev (SEQ ID NO: 69). The introduced glyoxylate reductase activity was confirmed by the standard glyoxylate reductase enzyme assay (the utilization of NADPH in the presence of glyoxylate). In contrast to the parental strain (An1015-acuEΔ::pyrG), An1015-acuEΔ::pyrG-GLYR1 had an increased glyoxylate reductase activity in crude extract.

Example 12. Production of Glycolic Acid by A. niger Strains

A. niger ATCC1015ΔacuE+GLYR1 was grown in the production medium (The defined medium of Vogel described by Mojzita et al. 2010) with 20 g glucose, xylose or ethanol l$^{-1}$ as a carbon source. Pre-cultures were grown in the medium containing 10 g yeast extract l$^{-1}$, 20 g peptone l$^{-1}$ and 30 g gelatine l$^{-1}$ (50 ml medium in 250 ml flasks). Mycelium from 50 ml cultures was collected by filtration, washed with sterile H$_2$O and re-suspended in 50 ml of the production medium in 250 ml flasks. Cultures were incubated at 30° C., 250 rpm. Culture supernatant was analysed by HPLC.

*A. niger* ATCC1015ΔacuE+GLYR/produced 0.5-100 g glycolic acid l$^{-1}$ extracellularly in 1-100 h. *A. niger* ATCC1015 (wild-type) and the parent strain (*A. niger* ATCC1015ΔacuE) produced no glycolic acid when grown under the same conditions.

Example 13. Other Possible Exogenous Glyoxylate Reductases Used for Glycolic Acid Production Instead of the *Arabidopsis thaliana* GLYR1 glyoxylate reductase it is possible to use any other glyoxylate reductase for glycolic acid production. According to our knowledge there are at the moment nine known glyoxylate reductases described in literature where the gene coding for the enzyme is known (Table 1). With BLAST search it is possible to look for genes with high homologies to these and get new possible candidates for glyoxylate reductases. The glyoxylate reductase gene of *Thermus thermophilus* (SEQ ID NO: 70) was ordered from GenScript with additional 5' BamHI and 3' EcoRI sites. The gene was introduced between the BamHI and EcoRI sites of the p2159 plasmid similarly as described in the case of *A. thaliana* GLYR1 in the Example 1A. The resulted vector was used in the strains described above and the strains were tested for glycolic acid production as described in the Example 9.

Example 14. Production of Glycolic Acid by Strain H3986 at pH 5.0 with High Yield

*K. lactis* strain H3986 was pregrown in flasks in modified synthetic complete (SC) medium lacking uracil (Sherman F, Fink G, Hicks J B. (1983) Methods in Yeast Genetics. A Laboratory Manual. Cold Springs Harbor Laboratory, Cold Springs Harbor, N.Y.). Glucose (20 g l$^{-1}$) was provided as carbon source. Pregrown cells were used for yeast cultivation started at OD$_{600}$=1 in a Biostat CT-DCU bioreactor (max. working volume 5000 ml, Sartorius, Göttingen, Germany) at pH 5.0, 30° C., 1 volume air [volume culture]$^{-1}$ min$^{-1}$ (vvm) and 500 rpm agitation with rushton turbines. Xylose (20 g l$^{-1}$) and ethanol (20 g l$^{-1}$) were provided as carbon source at the beginning of the fermentation. The pH was maintained constant by addition of 2 M NaOH. Silicone antifoaming agent (BDH, 0.2 ml l$^{-1}$) was added to prevent excess foaming. Xylose and ethanol were fed to the fermentor as separate feeds based on their consumption.

Extracellular metabolites in cell-free spent culture medium were analysed by capillary electrophoresis (P/ACE MDQ, Beckmann-Coulter) with UV detection according to Turkia et al. 2010.

H3986 produced extracellularly 17.2 g glycolic acid l$^{-1}$ after 9 days at pH 5.0 (Table 5). The yield of glycolic acid on xylose ethanol media was approximately 0.13 g glycolic acid [g ethanol+xylose]$^{-1}$ (Table 6).

TABLE 5

Glycolic acid production by strain H3986 at pH 5.0 in a fermentor.

Glycolic acid production ((g l$^{-1}$)

| Day 0 | Day 2 | Day 4 | Day 6 | Day 8 | Day 9 |
|---|---|---|---|---|---|
| 0 | 9.9 | 13.8 | 14.8 | 16.1 | 17.2 |

TABLE 6

Glycolic acid production yields by strain H3986.

| Yields based on accumulation (g/g) | |
|---|---|
| Glycolic acid/ethanol | 0.14 |
| Glycolic acid/ethanol + xylose | 0.13 |
| Biomass/xylose | 0.31 |
| Biomass/ethanol + xylose | 0.02 |

Example 15. Production of Glycolic Acid by Strain H3986 Using Acetate as Substrate

*K. lactis* strain H3986 was pregrown in flasks in modified synthetic complete (SC) medium lacking uracil (Sherman F, Fink G, Hicks J B. (1983) Methods in Yeast Genetics. A Laboratory Manual. Cold Springs Harbor Laboratory, Cold Springs Harbor, N.Y.). Glucose (20 g l$^{-1}$) was provided as carbon source. Pregrown cells were used for yeast cultivation started at OD$_{600}$=1 in a Biostat Q bioreactor (max. working volume 1000 ml, Satrorius, Göttingen, Germany) at pH 4.0, 30° C., 1 volume air [volume culture]$^{-1}$ min$^{-1}$ (vvm) and 500 rpm agitation with Rushton turbines. The pH was maintained constant by addition of 2 M NaOH. Silicone antifoaming agent (BDH, 0.2 ml l$^{-1}$) was added to prevent excess foaming. 5% xylose and 0.2% acetate were used as carbon sources and acetate was later on fed to the fermentor based on its consumption.

Extracellular metabolites in cell-free spent culture medium were analysed by capillary electrophoresis (P/ACE MDQ, Beckmann-Coulter) with UV detection according to Turkia et al. 2010. H3986 produced extracellularly 0.9 g glycolic acid l$^{-1}$ after 6 days at pH 4.0.

Example 16. Construction of a *K. lactis* Glycolic Acid Producing Strain with Increased NADPH Availability and Acetyl-CoA Synthase (ACS1) Overexpression Primer pair 234K1MLSflankTPIF (SEQ ID NO: 81), 235K1MLSflankURAR (SEQ ID NO: 82) was used to amplify *S. cerevisiae* aldehyde dehydrogenase, ALD6, gene which had been cloned to the p2159 plasmid (FIG. 3) under the TPI promoter. The 3.3 kb promoter-ALD6-terminator fragment and MLS flanks flanking upstream and downstream of the malate synthase gene of *K. lactis*. The fragment was transformed to the *K. lactis* strain H3976 (Table 2) and transformants were plated on SCD-URA plates.

Plasmid p4124 also known as pJJH955L (Heinisch J. et al. FEMS Yeast Res 10 (2010) 333-342) was used as a template for PCR with primer pair 236K1MLSURAflankLEUf (SEQ ID NO: 83), 237K1MLSflankLEUr (SEQ ID NO: 84). The 1.9 kb PCR product was then digested with NotI and ligated to the 2.3 kb fragment purified from the NotI digested p4124 plasmid. The constructed plasmid was digested by SalI.

*S. cerevisiae* acetyl-coenzyme A synthetase, ACS1, gene which had been cloned to the p609 plasmid (FIG. 8) under the mADH promoter was amplified by PCR by primer pair 240ACS_SalIF, 241ACS_SalIR. The 3.3 kb fragment was then digested by SalI and ligated with the above constructed and SalI digested vector. The resulting vector is overexpressing the *S. cerevisiae* ACS1 gene and having LEU marker between the loxP sites and having the flanks allowing integration to the MLS site of the above constructed *K. lactis* strain with ALD6 overexpression. The flanks were designed so that they also delete the URA marker introduced to the above constructed *K. lactis* strain with the ALD6 overexpression. The ACS1 overexpression cassette was digested by NotI and the 5.2 kb fragment was then transformed to the *K. lactis* (mls1Δ::ALD6, idp2Δ) strain. Transformants were plated on SCD-LEU plates.

Finally p4185 (described in Example 7) overexpressing GLYR1 was transformed to the strain and the transformants were plated on SCD-LEU-URA plates. The resulting strain is H4158. The strain was used for flask cultivations to compare glycolic acid production with the previously constructed strain H3986. Cultivations were done in 25 ml flasks on synthetic complete media (SC) lacking uracil (both strains) and leucine (only strain H4158) and having 2% xylose and 2% ethanol as carbon source. It was seen that in these conditions after three days of cultivation in +30° C. glycolic acid production of the strain H4158 was increased by 2.1 fold compared to the production of the H3986 strain grown in similar conditions. Glycolic acid production was analysed by HPLC as described in Example 9.

REFERENCES

Charbon G, Breunig K D, Wattiez R, Vandenhaute J, Noël-Georis I. (2004) Key role of Ser562/661 in Snf1-dependent regulation of Cat8p in *Saccharomyces cerevisiae* and *Kluyveromyces lactis*. Mol Cell Biol. 2004 May; 24(10): 4083-91.

Christianson T W, Sikorski R S, Dante M, Shero J H, Hieter P. (1992) Multifunctional yeast high-copy-number shuttle vectors. Gene. 1992 Jan. 2; 110(1):119-22.

Gietz and Woods (2002) Transformation of yeast by the LiAc/SS carrier DNA/PEG method. Methods in Enzymology 350: 87-96

Güldener U, Heck S, Fielder T, Beinhauer J, Hegemann J H. (1996) A new efficient gene disruption cassette for repeated use in budding yeast. Nucleic Acids Res. 1996 Jul. 1; 24(13): 2519-24.

Heinisch J J, Buchwald U, Gottschlich A, Heppeler N, Rodicio R. (2010) A tool kit for molecular genetics of *Kluyveromyces lactis* comprising a congenic strain series and a set of versatile vectors. FEMS Yeast Res. 2010 May; 10(3):333-42.

Hoover, G. J., Van Cauwenberghe, O. R., Breitkreuiz, K. E., Clark, S. M., Merrill, A. R., and Shelp, B. J. (2007). Characteristics of an *Arabidopsis* glyoxylate reductase: General biochemical properties and substrate specificity for the recombinant protein, and developmental expression and implications for glyoxylate and succinic semialdehyde metabolism in planta. Can. J. Bot. 85: 883-895.

Mojzita D, Wiebe M, Hilditch S, Boer H, Penttilä M, Richard P. (2010) Metabolic engineering of fungal strains for the conversion of D-galacturonate to meso-galactarate. *Appl Environ Microbiol* 2010, 76:169-175.

Ogino H, Nakayama H, China H, Kawata T, Doukyu N, Yasuda M. (2008) Characterization of recombinant glyoxylate reductase from thermophile *Thermus thermophilus* HB27. Biotechnol Prog. 2008 March-April; 24(2): 321-5. Epub 2008 Feb. 27.

Sambrook et al. (1989)

Sambrook and Russell (2001)

Sherman F, Fink G, Hicks J B. (1983) Methods in Yeast Genetics. A Laboratory Manual. Cold Springs Harbor Laboratory, Cold Springs Harbor, N.Y.

Turkia H, Sirén H, Pitkänen J P, Wiebe M, Penttilä M. (2010) Capillary electrophoresis for the monitoring of carboxylic acid production by *Gluconobacter oxydans*. J. Chromatogr. A., 1217 (2010) 1537-1542.

Voth W P, Richards J D, Shaw J M, Stillman D J. (2001) Yeast vectors for integration at the HO locus. Nucleic Acids Res. 2001 Jun. 15; 29(12):E59-9.

The invention claimed is:

1. A eukaryotic production host selected from yeast and filamentous fungus cell of species *Saccharomyces cerevisiae, Kluveromyces lactis, Candida krusei* and *Aspergillus niger*, wherein the host:
   has been genetically modified by transformation of a protein-encoding polynucleotide into the genome of the host cell,
   expresses a heterologous gene encoding the glyoxylate reductase of SEQ ID NO: 3, and
   produces glycolic acid at a pH of 1.5 to 6.0,
wherein glyoxylate pathway flux has been increased:
   a) by overexpressing one or more of the genes selected from isocitrate lyase, fumarate reductase, aconitase, citrate synthase and acetyl-coenzyme A synthetase; or
   b) by reducing activity of the enzymes consuming the intermediates of the cycle; or
   c) any combination of a) and b).

2. The host of claim 1, which is capable of producing glycolic acid in non-buffered culturing conditions.

3. The host of claim 1, wherein the glyoxylate reductase gene encodes a protein having EC number 1.1.1.79 or 1.1.1.26.

4. The host of claim 3, wherein the cells of the host comprise the genes encoding proteins of SEQ ID NO: 3.

5. A eukaryotic production host selected from yeast and filamentous fungus cell of species *Saccharomyces cerevisiae, Kluveromyces lactis, Candida krusei* and *Aspergillus niger*, wherein the host:
   has been genetically modified by transformation of a protein-encoding polynucleotide into the genome of the host cell,
   expresses a heterologous gene encoding the glyoxylate reductase of SEQ ID NO: 3, and
   produces glycolic acid at a pH of 1.5 to 6.0,
wherein glyoxylate cycle regulating gene REG1 has been attenuated or CAT8 has been activated.

6. A eukaryotic production host selected from yeast and filamentous fungus cell of species *Saccharomyces cerevisiae, Kluveromyces lactis, Candida krusei* and *Aspergillus niger*, wherein the host:
   has been genetically modified by transformation of a protein-encoding polynucleotide into the genome of the host cell,
   expresses a heterologous gene encoding the glyoxylate reductase of SEQ ID NO: 3, and
   produces glycolic acid at a pH of 1.5 to 6.0,
wherein alcohol production has been reduced by:
   a) overexpressing one or more of pyruvate carboxylases; or
   b) reducing expression of gene encoding alcohol dehydrogenase.

7. A eukaryotic production host selected from yeast and filamentous fungus cell of species *Saccharomyces cerevisiae, Kluveromyces lactis, Candida krusei* and *Aspergillus niger*, wherein the host:
   has been genetically modified by transformation of a protein-encoding polynucleotide into the genome of the host cell,
   expresses a heterologous gene encoding the glyoxylate reductase of SEQ ID NO: 3, and
   produces glycolic acid at a pH of 1.5 to 6.0,
wherein NADPH availability has been improved by overexpressing cytosolic aldehyde dehydrogenase gene or deleting phosphoglucose isomerase gene.

* * * * *